(12) United States Patent
Macary et al.

(10) Patent No.: US 9,376,486 B2
(45) Date of Patent: Jun. 28, 2016

(54) HUMAN MONOCLONAL ANTIBODY WITH SPECIFICITY FOR DENGUE VIRUS SEROTYPE 1 E PROTEIN AND USES THEREOF

(75) Inventors: Paul Anthony Macary, Singapore (SG); Ee Ping Evelyn Teoh, Singapore (SG); Brendon John Hanson, Singapore (SG); En Wei Teo, Singapore (SG); Angeline Pei Chiew Lim, Singapore (SG); Mah Lee Mary Ng, Singapore (SG); Shee Mei Lok, Singapore (SG); Petra Eveliina Kukkaro, Singapore (SG)

(73) Assignees: National University of Singapore, Singapore (SG); DSO National Laboratories, Singapore (SG)

( * ) Notice: Subject to any disclaimer, the term of this patent is extended or adjusted under 35 U.S.C. 154(b) by 0 days.

(21) Appl. No.: 13/993,983

(22) PCT Filed: Dec. 14, 2011

(86) PCT No.: PCT/SG2011/000436
§ 371 (c)(1),
(2), (4) Date: Jun. 13, 2013

(87) PCT Pub. No.: WO2012/082073
PCT Pub. Date: Jun. 21, 2012

(65) Prior Publication Data
US 2013/0259871 A1 Oct. 3, 2013

Related U.S. Application Data

(60) Provisional application No. 61/423,085, filed on Dec. 14, 2010.

(51) Int. Cl.
| | | |
|---|---|---|
| C07K 16/10 | (2006.01) | |
| A61K 39/42 | (2006.01) | |
| A61K 45/06 | (2006.01) | |
| A61K 39/00 | (2006.01) | |

(52) U.S. Cl.
CPC .............. *C07K 16/1081* (2013.01); *A61K 39/42* (2013.01); *A61K 45/06* (2013.01); *A61K 2039/505* (2013.01); *C07K 2317/21* (2013.01); *C07K 2317/34* (2013.01); *C07K 2317/55* (2013.01); *C07K 2317/565* (2013.01); *C07K 2317/76* (2013.01)

(58) Field of Classification Search
CPC ....................... C07K 16/1081; C07K 2317/565
See application file for complete search history.

(56) References Cited

U.S. PATENT DOCUMENTS

2009/0074781 A1  3/2009  Chen et al.

FOREIGN PATENT DOCUMENTS

| WO | 03080672 | 10/2003 |
| WO | 2005056600 | 6/2005 |
| WO | 2010043977 | 4/2010 |
| WO | 2010093335 | 8/2010 |

OTHER PUBLICATIONS

Chen, C., et al., Sep. 1992, Generation and analysis of random point mutations in an antibody CDR2 sequence: many mutated antibodies lose their ability to bind antigen, J. Exp. Med. 176:855-866.*
Xiang, J., et al., 1995, Framework residues 71 and 93 of the chimeric B72.3 antibody are major determinants of the conformation of heavy-chain hypervariable loops, J. Mol. Biol. 253:385-390.*
Schieffelin, J. S., et al., 2010, Neutralizing and non-neutralizing monoclonal antibodies against dengue virus E protein derived from a naturally infected patient, Virol. J. 7(28):1-11.*
Beltramello, M., et al., Sep. 2010, The human immune response to dengue virus is dominated by highly cross-reactive antibodies endowed with neutralizing and enhancing activity, Cell Host Microbe 8:271-283.*
CA2,821,268, Office Action, Jul. 7, 2014, 4 pages.
CN201180066887.9, Office Action, Nov. 28, 2014, 7 pages.
EP11848839.4, Extended European Search Report, Apr. 17, 2014, 9 pages.
PCT/SG2011/000436, International Search Report and Written Opinion, Mar. 2, 2012, 9 pages.
Lok et al., "Binding of a neutralizing antibody to dengue virus alters the arrangement of surface glycoproteins", Nature Structural & Molecular Biology, vol. 15, No. 3, Feb. 10, 2008, pp. 312-317.
Ping et al., "The Structural Basis 1-15 for Serotype-Specific Neutralization of Dengue Virus by a Human Antibody", Science Translational Medicine. vol. 4. No. 139, Jun. 2012.
Rudikoff et al., "Single Amino Acid Substitution altering Antigen-binding Specificity", Proc. Natl Acad Sci., 1982, pp. 1979-1983.
Shrestha et al., "The Development of Therapeutic Antibodies That Neutralize Homologous and Heterologous Genotypes of Dengue Virus Type 1", PLoS Pathogens, vol. 6, No. 4, Apr. 1, 2010, e1000823.
Tamura et al., "Structural Correlates of an Anticarcinoma Antibody: Identification of Specificity-Determining Residues (SDRs) and Development of a Minimally Immunogenic Antibody Variant by Retention of SDRs Only", J. Immunol., 164, 2000, pp. 1432-1441.
Zou et al., "Resistance analysis of an antibody that selectively inhibits dengue virus serotype-1", Antiviral Research. vol. 95. No. 3, Sep. 1, 2012, pp. 216-223.

* cited by examiner

*Primary Examiner* — Jeffrey Parkin
(74) *Attorney, Agent, or Firm* — Kilpatrick Townsend & Stockton LLP

(57) ABSTRACT

Compositions and methods for the treatment or prevention of Dengue virus infection in a vertebrate subject are provided. In particular, human neutralizing monoclonal antibodies to Dengue virus isolated from EBV immortalized B cells derived from patients who have recovered from Dengue infection are disclosed. Methods are provided for administering such antibodies to a vertebrate subject in an amount effective to reduce, eliminate, or prevent relapse from infection.

19 Claims, 26 Drawing Sheets

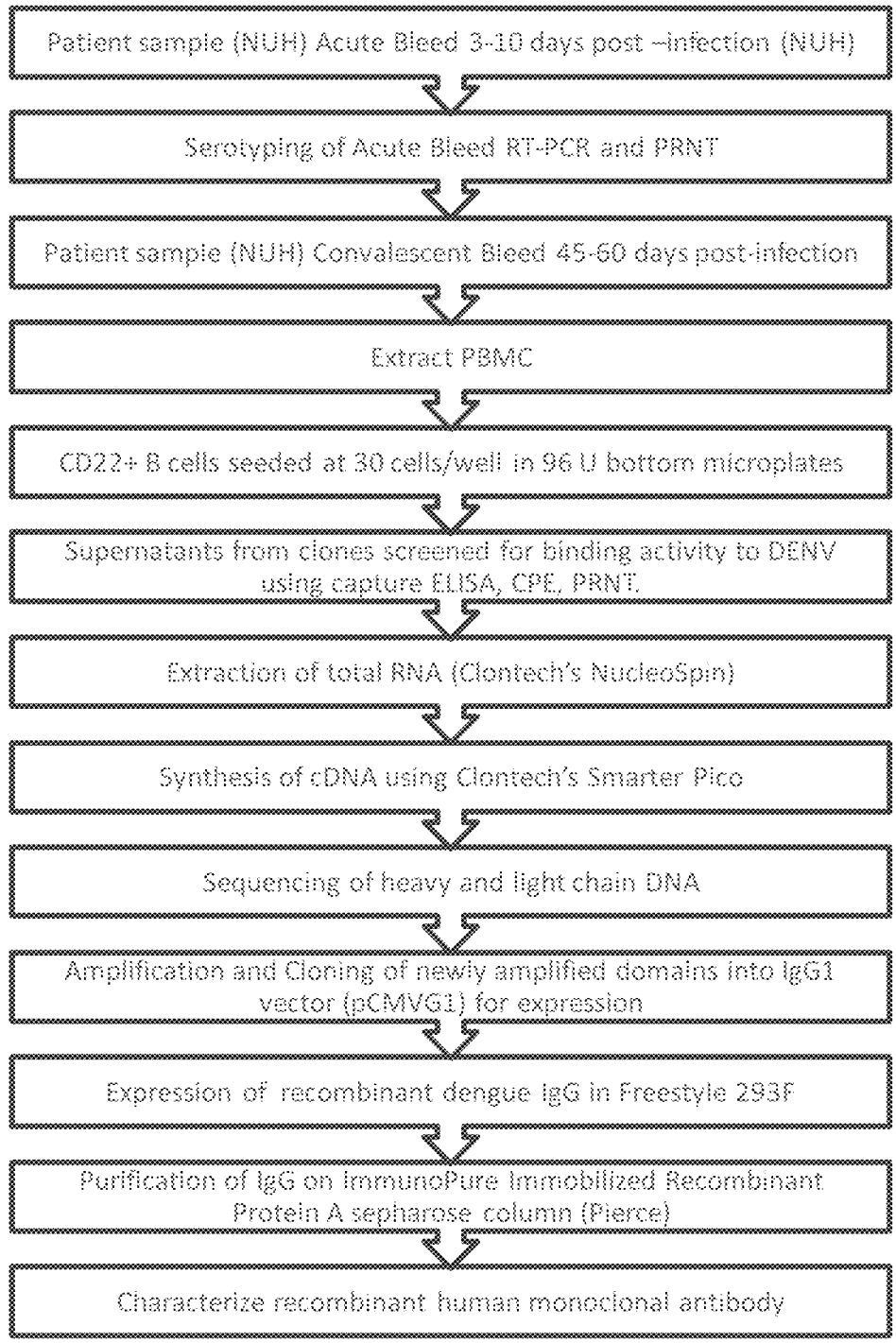
Figure 1: Flowchart of the process of antibody screening, expression and characterization

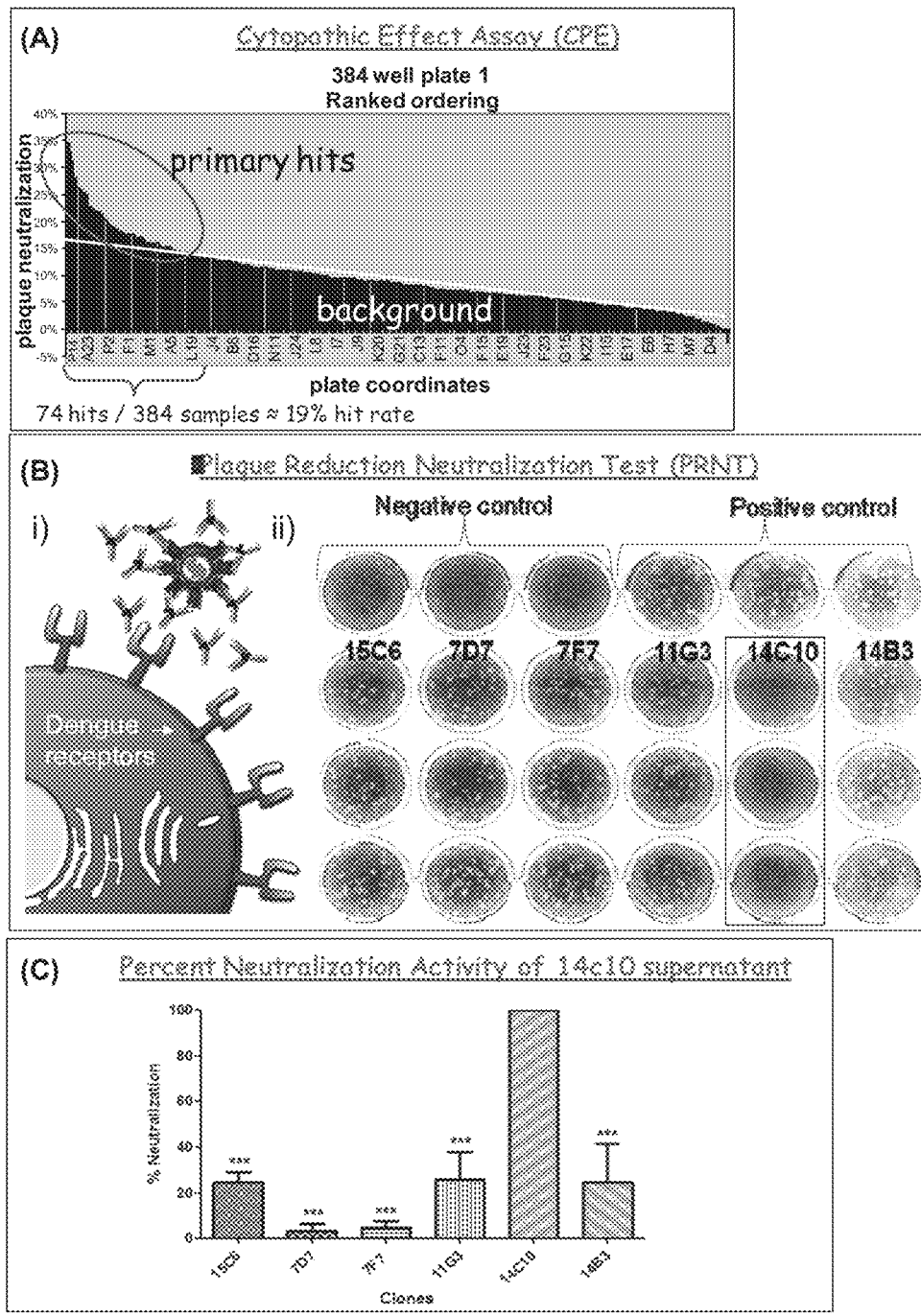
Figure 2: Screening of supernatants from immortalized B cell clones by CPE and PRNT assay.

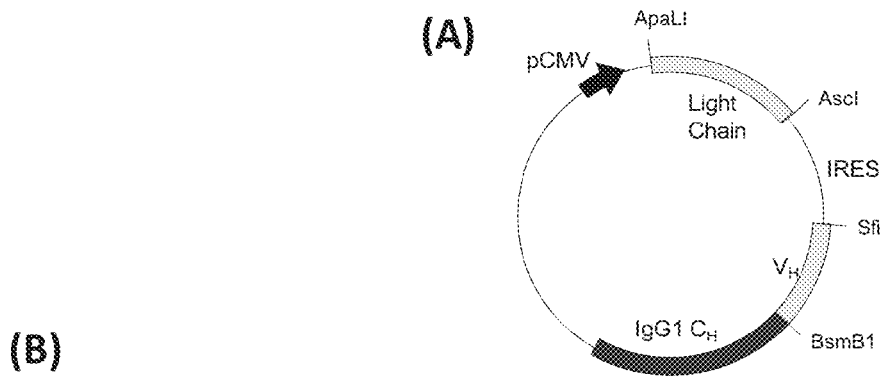

(A)

(B)

| Clone | Light Chain Sequence | Heavy Chain Sequence |
|---|---|---|
| 1 | DIVMTQSPLSLSVTPGQPASISCRSSQSLLHSDGRTSLDWFLLRPGQFPQVKISELSRRFSGVPDRVSGSGSGTDFTLKISRGEAEDVRAFYCIYGIYVGRSAKGPSWRSN | QVQLVQSGAEVKKPGTSVKVSCKASGYNFTDYYVHWVRQAPGQGLEWMAWINPNSGGSKYAQMFQGRISLTRDTSISTAYLELFSLTSDDTAVYYCADLTAEDVWGQGTLVTVSSGTTVTVSS |
| 2 | DIVMTQSPLSLSVTPGQPASISCRSSQSLLHSDGRTSLDWFLLRPGQFPQVKISELSRRFSGVPDRVSGSGSGTDFTLKISRGEAEDVRAFYCIYGIYVGRSAKGPSWRSN | EVQLVESGGGVVQPGRSLRLSCAASGFSFSSYGMHWVRQAPGKGLEWVAVIWYDGSKTYYGDSVKGRFTISKDNSKKMVNLQMDSLGVEDTAFYYCARGIAGGWAFWGIDLWGQGTLVTVSS |
| 3 | DIVMTQSPLSLSVTPGQPASISCRSSQSLLHSDGRTSLDWFLLRPGQFPQVKISELSRRFSGVPDRVSGSGSGTDFTLKISRGEAEDVRAFYCIYGIYVGRSAKGPSWRSN | EVQLVQSGGGVVRPGKSLRLSCAASGFTFDDYGMSWVRQAPGKGLEWVSGINWNGGSTGYADSVKGRFTISRDNAKNSLYLQMNSLRAEDTAFYYCAREYGSGSYINWFDPWGQGTLVTVSS |
| 4 | DIQMTQSPLSLPVTPGEPASISCRSSQSLLHTNGNNYLDWYLQKPGQSPQLLIYLGSNRASGVPDRFSGSGSGTDFTLKISRVEAEDVGVYYCVQALQTKTTFGQGTKLEIKR | QVQLVQSGAEVKKPGTSVKVSCKASGYNFTDYYVHWVRQAPGQGLEWMAWINPNSGGSKYAQMFQGRISLTRDTSISTAYLELFSLTSDDTAVYYCADLTAEDVWGQGTLVTVSSGTTVTVSS |
| 5 | DIQMTQSPLSLPVTPGEPASISCRSSQSLLHTNGNNYLDWYLQKPGQSPQLLIYLGSNRASGVPDRFSGSGSGTDFTLKISRVEAEDVGVYYCVQALQTKTTFGQGTKLEIKR | EVQLVESGGGVVQPGRSLRLSCAASGFSFSSYGMHWVRQAPGKGLEWVAVIWYDGSKTYYGDSVKGRFTISKDNSKKMVNLQMDSLGVEDTAFYYCARGIAGGWAFWGIDLWGQGTLVTVSS |
| 6 | DIQMTQSPLSLPVTPGEPASISCRSSQSLLHTNGNNYLDWYLQKPGQSPQLLIYLGSNRASGVPDRFSGSGSGTDFTLKISRVEAEDVGVYYCVQALQTKTTFGQGTKLEIKR | EVQLVQSGGGVVRPGKSLRLSCAASGFTFDDYGMSWVRQAPGKGLEWVSGINWNGGSTGYADSVKGRFTISRDNAKNSLYLQMNSLRAEDTAFYYCAREYGSGSYINWFDPWGQGTLVTVSS |
| 7 | DIVMTQSPGTLSLSPGERATLSCRASQNVYSYLGWYQHKPGRSPRLLIFGVTSRATGVPDRFSGSGSGTDFTLTISRLEPEDFAVYYCQQYAGSAYTFGQGTKVEIK | QVQLVQSGAEVKKPGTSVKVSCKASGYNFTDYYVHWVRQAPGQGLEWMAWINPNSGGSKYAQMFQGRISLTRDTSISTAYLELFSLTSDDTAVYYCADLTAEDVWGQGTLVTVSSGTTVTVSS |
| 8* | DIVMTQSPGTLSLSPGERATLSCRASQNVYSYLGWYQHKPGRSPRLLIFGVTSRATGVPDRFSGSGSGTDFTLTISRLEPEDFAVYYCQQYAGSAYTFGQGTKVEIK | EVQLVESGGGVVQPGRSLRLSCAASGFSFSSYGMHWVRQAPGKGLEWVAVIWYDGSKTYYGDSVKGRFTISKDNSKKMVNLQMDSLGVEDTAFYYCARGIAGGWAFWGIDLWGQGTLVTVSS |
| 9 | DIVMTQSPGTLSLSPGERATLSCRASQNVYSYLGWYQHKPGRSPRLLIFGVTSRATGVPDRFSGSGSGTDFTLTISRLEPEDFAVYYCQQYAGSAYTFGQGTKVEIK | EVQLVQSGGGVVRPGKSLRLSCAASGFTFDDYGMSWVRQAPGKGLEWVSGINWNGGSTGYADSVKGRFTISRDNAKNSLYLQMNSLRAEDTAFYYCAREYGSGSYINWFDPWGQGTLVTVSS |
| 10 | DIVMTQSPDSLAVSLGERATINCKSSQSVLHSSNNKNYLAWYQQKPGQPPKLLIYWASTRESGVPDRFSGSGSGTDFTLTISSLQAEDVAVYYCQQYYSAPHKFGQGTKLEIK | QVQLVQSGAEVKKPGTSVKVSCKASGYNFTDYYVHWVRQAPGQGLEWMAWINPNSGGSKYAQMFQGRISLTRDTSISTAYLELFSLTSDDTAVYYCADLTAEDVWGQGTLVTVSSGTTVTVSS |
| 11 | DIVMTQSPDSLAVSLGERATINCKSSQSVLHSSNNKNYLAWYQQKPGQPPKLLIYWASTRESGVPDRFSGSGSGTDFTLTISSLQAEDVAVYYCQQYYSAPHKFGQGTKLEIK | EVQLVESGGGVVQPGRSLRLSCAASGFSFSSYGMHWVRQAPGKGLEWVAVIWYDGSKTYYGDSVKGRFTISKDNSKKMVNLQMDSLGVEDTAFYYCARGIAGGWAFWGIDLWGQGTLVTVSS |
| 12 | DIVMTQSPDSLAVSLGERATINCKSSQSVLHSSNNKNYLAWYQQKPGQPPKLLIYWASTRESGVPDRFSGSGSGTDFTLTISSLQAEDVAVYYCQQYYSAPHKFGQGTKLEIK | EVQLVQSGGGVVRPGKSLRLSCAASGFTFDDYGMSWVRQAPGKGLEWVSGINWNGGSTGYADSVKGRFTISRDNAKNSLYLQMNSLRAEDTAFYYCAREYGSGSYINWFDPWGQGTLVTVSS |

Figure 3: Identification and recombinant expression of antibody Heavy and Light Chain Templates from B-cell line 14c10.

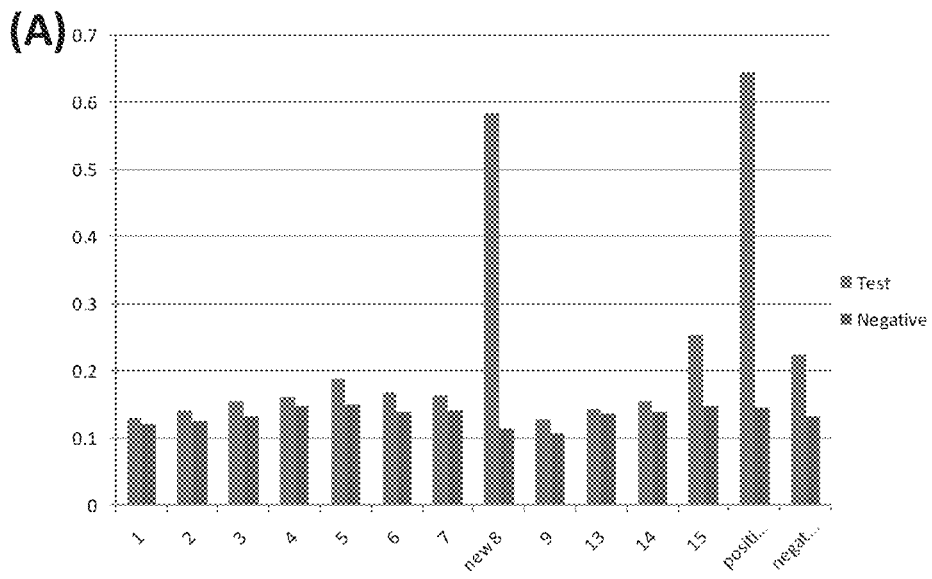
Figure 4: Recombinant antibody no: 8 from B cell line 14C10 has neutralizing activity for Dengue serotype 1.

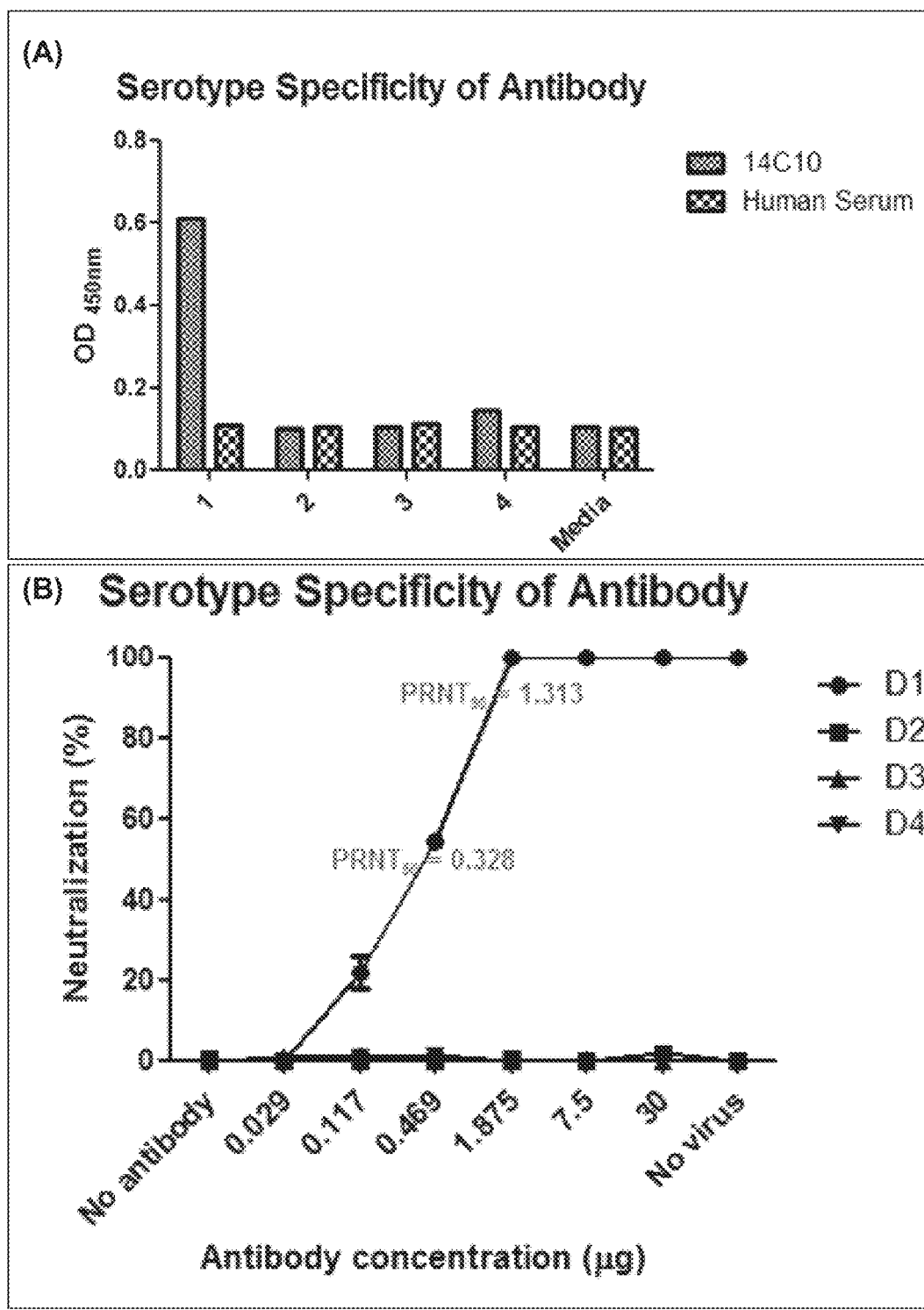
Figure 5: Serotype specificity of recombinant 14C10.8 antibody tested by PRNT and ELIZA.

(C)
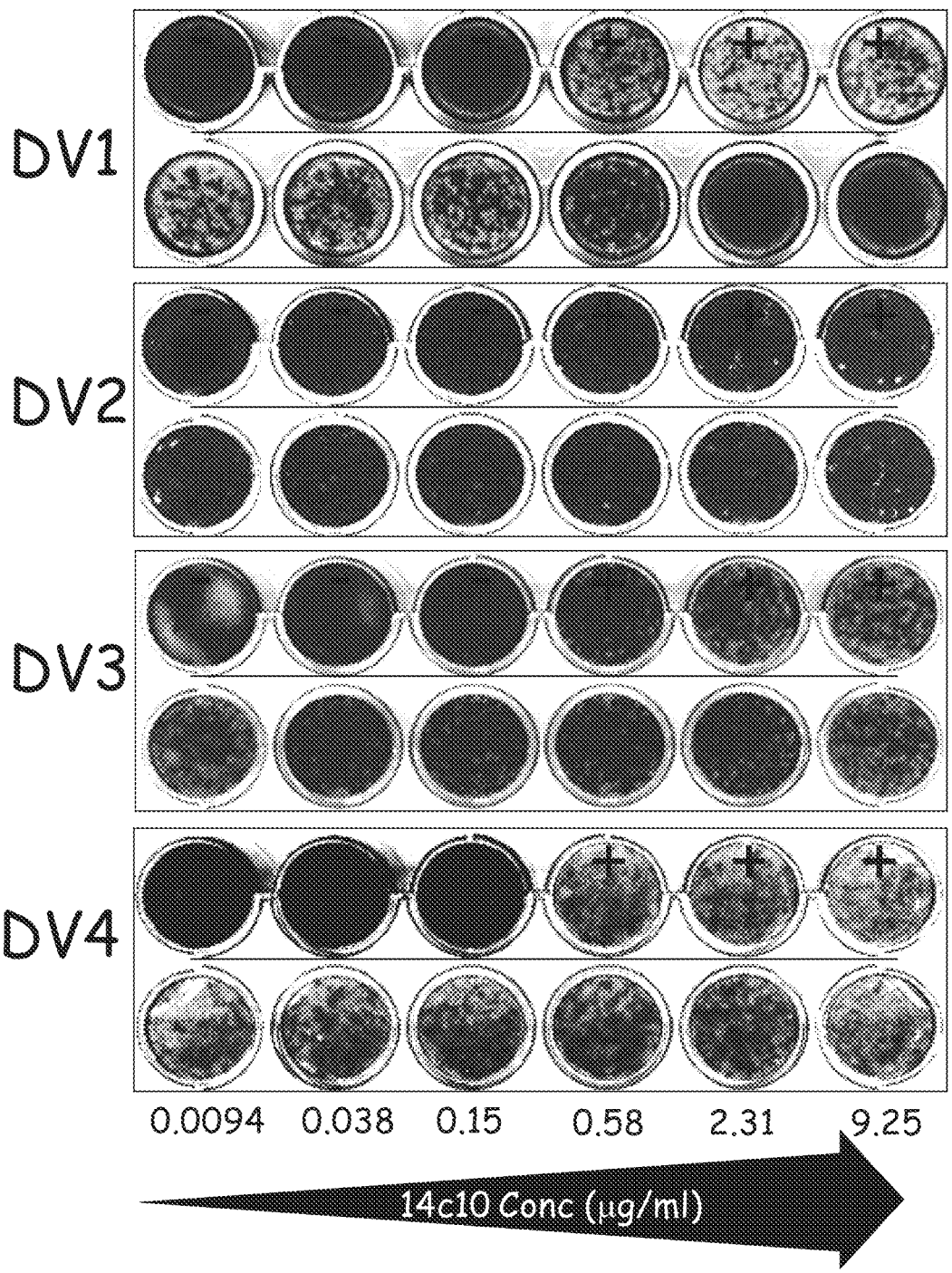
Figure 5 contd: Serotype specificity of recombinant 14C10.8 antibody with PRNT and ELIZA.

– – – – = No Antibody Control      =Enhanced Infection

Figure 6: In vitro Antibody Dependent Enhancement of Dengue serotype 1, 2, 3 and 4 infection of K562 Cells by 14c10 Versus 4G2.

Figure 7: In vitro Antibody Dependent Enhancement of Dengue serotype 1, infection of K562 Cells by 14c10.8 Expressed as recombinant human IgG1, IgG3 or IgG4.

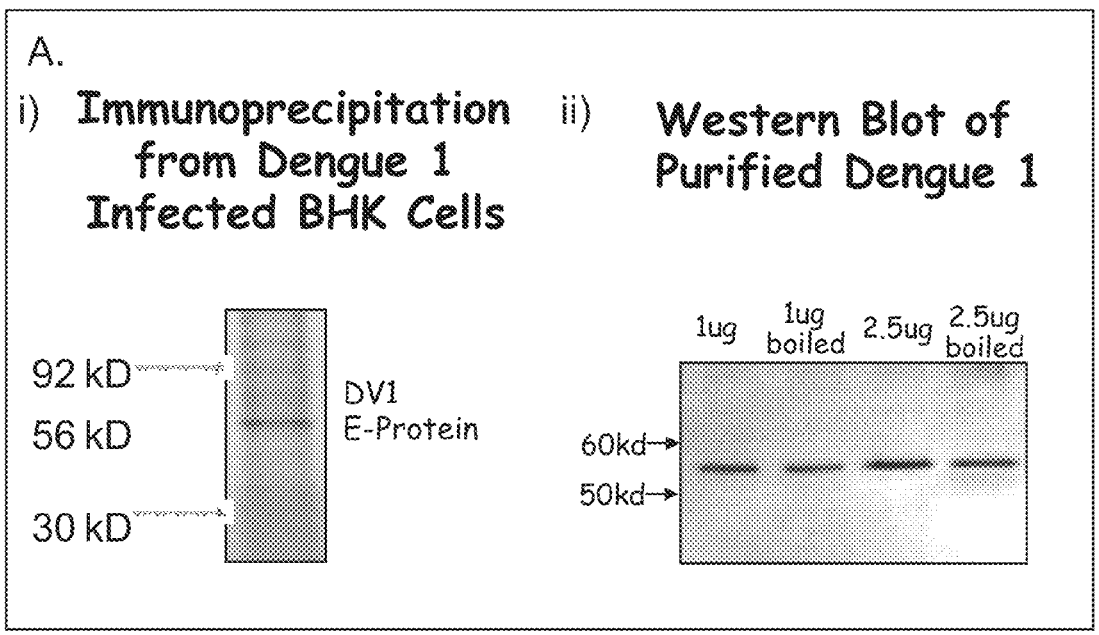
Figure 8: 14c10.8 is specific for a linear epitope on Dengue Serotype 1 E-Protein

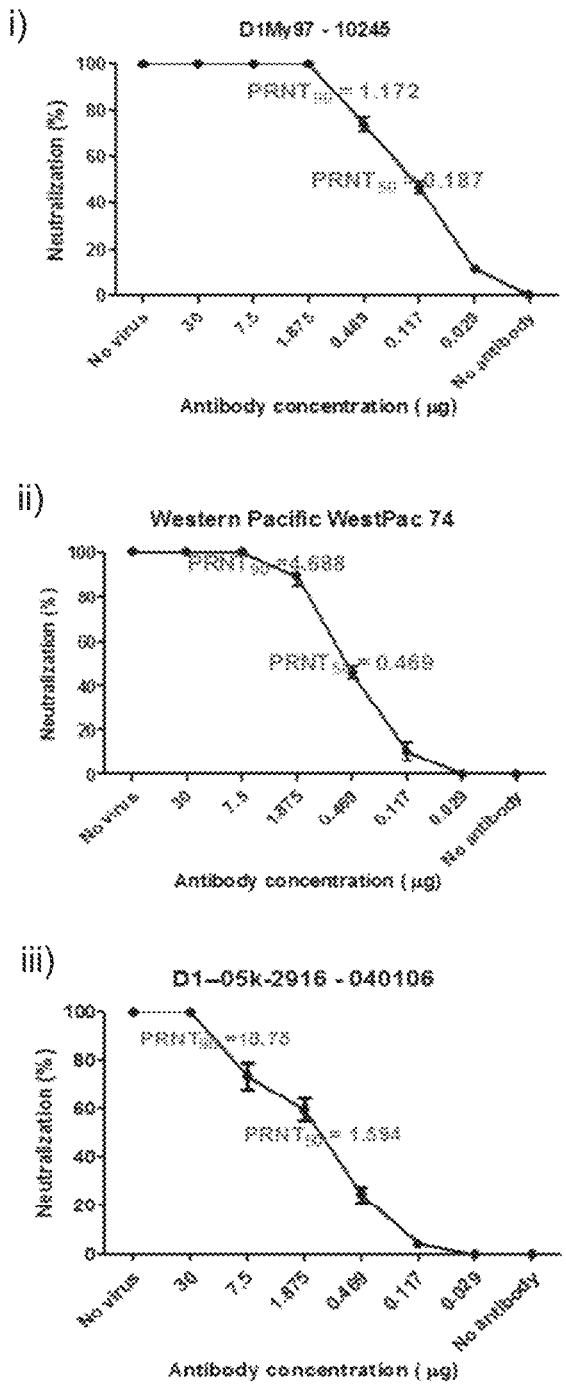
Figure 9: Neutralization activity of recombinant 14c10 against various genotypes.

iv)

Hawaii

PRNT₉₀ ~ 16.5

PRNT₅₀ ~ 5.25

Antibody concentration (μg)

AF425619:

MRCVGIGNRDFVEGLSGATWVDVVLEHGSCVTTMAK
DKPTLDIELLKTEVTNPAVLRKLCIEAKISNTTTDSRCPT
QGEATLVEEQDANFVCRRTFVDRGWGNGCGLFGKGS
LITCAKFKCVTKLEGKIVQYENLKYSVIVTVHTGDQHQV
GNETTEHGTIATITPQAPTSEIQLTDYGALTLDCSPRTG
LDFNEMVLLTMKEKSWLVHKQWFLDLPLPWTSGAST
PQETWNREDLLVTFKTAHAKKQEVAVLGSQEGAMHT
ALTGATEIQTSGTTKIFAGHLKCRLKMDRLTLKGMSYV
MCTGSFKLEKEVAETQHGTVLVQVKYEGTDAPCKIPFS
TQDEKGVTQNGRLITANPIVTDKEKPVNIEAEPPFGESY
IVVGAGEKALKLSWFKKGSSIGKMLEATARGARRMAI
LGDTAWDFGSIGGVFTSVGKLVHQIFGTAYGVLFSGV
SWTMKIGIGILLTWLGLNSRSASLSMTCIAVGMVTLYL
GVMVQA v)

Ehi D1

PRNT₉₀ ~ 1.313

PRNT₅₀ ~ 0.328

Antibody concentration (μg)

GQ357687:

MRCVGIGSRDFVEGLSGATWVDVVLEHGSCVTTMA
KDKPTLDIELLKTEVTNPAVLRKLCIEAKISNTTTDSRC
PTQGEATLVEEQDANFVCRRTFVDRGWGNGCGLFG
KGSLITCAKFKCVTKLEGKIVQYENLKYSVIVTVHTGD
QHQVGNESTEHGTTATITPQAPTTEIQLTDYGALTLD
CSPRTGLDFNEMVLLTMKEKSWLVHKQWFLDLPLP
WTSGASTSQETWNRQDLLVTFKTAHAKKQEVVVLG
SQEGAMHTALTGATEIQTSGTTTIFAGHLKCRLKMDK
LTLKGMSYVMCTGSFKLEKEVAETQHGTVLVQIKYE
GTDAPCKIPFSTQDEKGVTQNGRLITANPIVTDKEKP
VNIEAEPPFGESYIVIGAGEKALKLSWFKKGSSIGKM
FEATARGARRMAILGDTAWDFGSIGGVFTSVGKLVH
QIFGTAYGVLFSGVSWTMKIGIGVLLTWLGLNSRST
SLSMTCIAVGLVTLYLGVMVQA

Figure 9 contd: Neutralization activity of recombinant 14c10.8 against various genotypes.

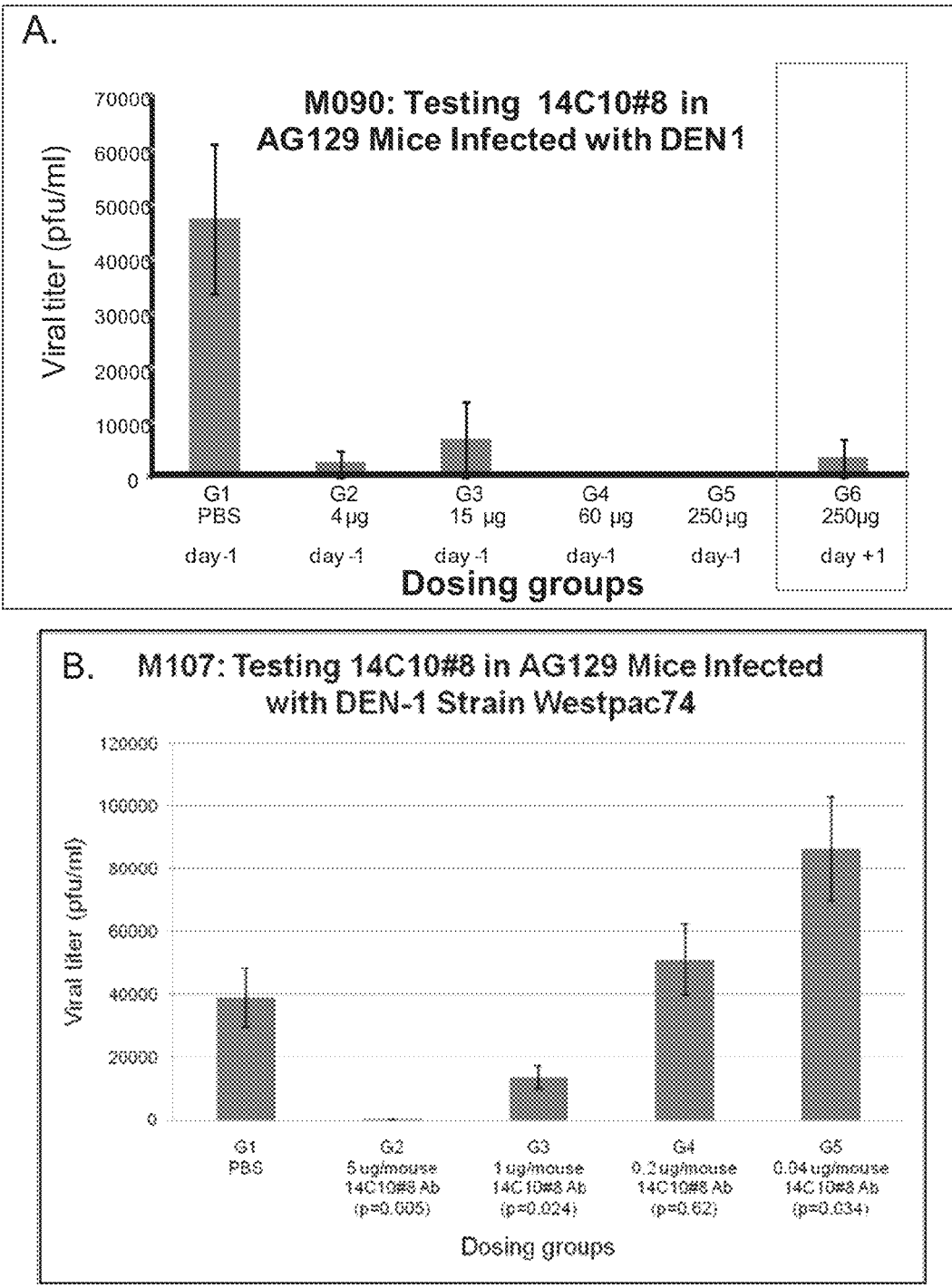
Figure 10: 14c10.8 has prophylactic and therapeutic activity *in vivo*.

Identification and recombinant expression of a fully human antibody with neutralizing activity for Dengue Virus.

HM14c10 exhibits binding activity for multiple DENV1 clinical isolates.

Fit of the post-fusion crystal structure of DENV1 E proteins into the cryoEM map of Fab HM14c10 complexed with Dengue 1 virus.

Stereo-diagram of the Fab HM14c10 and E protein binding interface.

Superposition of the variable regions of homology model of HM14c10 (green) with reference human monoclonal antibody (PDB code 2GHW) (blue). Figure is showing (A) side and (B) top view of the antibody variable regions.

A

B

| Fab position | Fab density | Antibody chain | Number of fitted atoms / number of atoms outside contour after fitting | Average map value at atom positions after fitting |
|---|---|---|---|---|
| I | a | light | 834 / 584 | 2.077 |
|   | b | heavy | 936 / 663 | 2.074 |
| I | a | heavy | 936 / 666 | 1.791 |
|   | b | light | 834 / 580 | 2.117 |
| II | a | light | 834 / 533 | 2.286 |
|   | b | heavy | 936 / 676 | 1.936 |
| II | a | heavy | 936 / 640 | 2.022 |
|   | b | light | 834 / 629 | 1.909 |

Fitting of the homology model of HM14c10 variable region into HM14c10:DENV1 cryoEM density map.

Figure 20A

HM14c10 epitope on dengue serotype 1 (genotype PVP159) and comparison of the epitope with (A) other DENV1 genotypes and (B) dengue serotypes and West Nile virus (WNV).

Figure 20A

| | | |
|---|---|---|
| DENV1 Hawaii | MRCVGIGNRDFVEGLSGATWVDVVLEHGSCVTTMAKDKPTLDIELLKTEVTNPAVLRKLCIEAKISNTTTDSRCPTQGEATLVEEQDANFVCRRTFVDRG | 100 |
| DENV3 H87 | MRCVGVGNRDFVEGLSGATWVDVVLEHGGCVTTMAKNKPTLDIELQKTEATLATLRKLCIEGKITNITTDSRCPTQGEAILPEEQDQNYVCKRTVVDRG | 100 |
| DENV2 NGC | MRCIGISNRDFVEGVSGGSWVDIVLEHGSCVTTMAKNKPTLDFELIKTEAKQPATLRKYCIEAKLTNTTTDSRCPTQGEPSLNEEQDKRFVCKRSMVDRG | 100 |
| DENV4 H241 | MRCVGVGNRDFVEGVSGQAWVDLVLEHGSCVTTMAQGKPTLDFELIKTTAKEVALLRTYCIEASISNITTATRCPTQGEPYLKEEQDQQYICRRDVVDRG | 100 |
| WNV NY99 | FNCLGMSMRDFLEGVSGATWVDLVLEGDSCVTIMSKDKPTIDVKMMNKEAALAEVRSYCYLATVSDLSTKAACPTMGEAHNKRADPAFVCRQGVVDRG | 100 |

| | | |
|---|---|---|
| DENV1 Hawaii | WGNGCGLFGKGSLITCAKFKCVTKLEGKIVQYENLKYSVIVTVHT-GDQHQVGNETTETHQAPTSELEDYGALTLDCSPRTGLDFNE | 195 |
| DENV3 H87 | WGNGCGLFGKGSLVTCAKFQCLESIEGKVVQHENLKYTVIITPHS-GDQHQVGNERQYTAEHLPKYCTIGLECSPRTGLDFNE | 193 |
| DENV2 NGC | WGNGCGLFGKGGIVTCAMFTCKKNMGKVVQPENLEYTIVITPHS-GEEHAVGNDTGKHGKEIKTPQSSITHLPGVCTVTMECSPRTGLDFNE | 195 |
| DENV4 H241 | WGNGCGLFGKGGVVTCAKFSCSGKITGNLVQRENLKYTVVTVHN-GDTHAVGNDIPNHRFTARTPQSPSVELEDYGELTLDCEPRSGIDFNE | 195 |
| WNV NY99 | WGNGCGLFGKGSIDTCAKFACSTKAIGRTILKENIKYEVAIFVHGPTTVESHGNYSTQVKATQAGRLSTTPAAPSYTLKLGEYGEVTVDCEPRSGIDTNA | 200 |

| | | |
|---|---|---|
| DENV1 Hawaii | MVLLTMKEKSWLVHKQWFLDLPLPWTSGASTPQETWNREDLLVTFKTAHAKKQEVAVLGSQEGAMHTALTGATEIQTSGTTKIFAGHLKCRLKMDKLTL | 294 |
| DENV3 H87 | MVLLTMKNKAWMVHRQWFFDLPLPWTSGATTETPTWNRKELLVTFKNAHAKKQEVVVLGSQEGAMHTALTGATEIQTSGTTSIFAGHLKCRLLMDKIKL | 292 |
| DENV2 NGC | MVLLQMENKAWLVHRQWFIDLPLPWLPGADTQGSNWIQKETLVTFKNPHAKKQDVVVLGSQEGAMHTALTGATEIQNSS--GNLLFTGHLKCRLKMDKLQL | 294 |
| DENV4 H241 | MILMKMKKKTWLVHKQWFLDLPLPWAAGADTSEVHWNYKERMVTFKVPHAKRQDVTVLGSQEGAMHSALTGATEVDSGD-GNHMFAGHLKCRVRMEKLRI | 294 |
| WNV NY99 | YYPMTVGTKTFLVHREWFMDLNLPWSSAGST---VFNRRETLMEFEEPHATKQSVIALGSQEGALHQALAGAIPVEFSSNTVKLTSGHLKCRVKMEKLQL | 297 |

| | | |
|---|---|---|
| DENV1 Hawaii | KGMSYVMCTGSFKLEKVAAETQHGTVLVQVKYEGTDAPCKIPFS--TQDEKGVTQNGRLITANPIVTDKEKPVNIEAEPPFGESYIVVGAGEKALKLSWFKRGS | 396 |
| DENV3 H87 | KGMSYAMCLNTFVLKKEVSETQHGTILIKVEYKGEDAPCKIPFS--TEDGQGKAHNGRLITANPVVTKKEEPVNIEAEPPFGESNIVIGIGDKALKIMNWYKRGS | 394 |
| DENV2 NGC | KGMSYSMCTGKFKVVKEIAETQHGTVIRVQYEGDGSPCKIPFE--IMDLEKRHVLGRLITVNPIVTEK--DSPVNIEAEPPFGDSYIIIGVEPGQLRLNWFKKGS | 396 |
| DENV4 H241 | KGMSYTMCSGKFSIKMAETQHGTVVKVKYEGAGAPCKVPIE--IRDVNKEKVVGRIISSTPFAEYT--NSVTNIELEPPFGDSYIVIGVGSALTLHWFRKGS | 396 |
| WNV NY99 | KGTTYGVCSKAFKFLGTPADTGHGTVVLELQYTGTDGPCKVPISSVASLNDLTPVGRLVTVNPFVSVATANARVLIELEPPFGDSYIVVGRGEQINHHWHKSGS | 402 |

HM14c10 epitope on dengue serotype 1 (genotype PVP159) and comparison of the epitope with (A) other DENV1 genotypes and (B) dengue serotypes and A
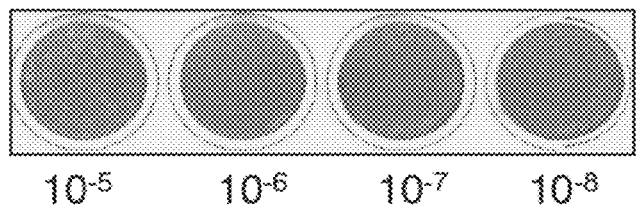
$10^{-5}$    $10^{-6}$    $10^{-7}$    $10^{-8}$
B
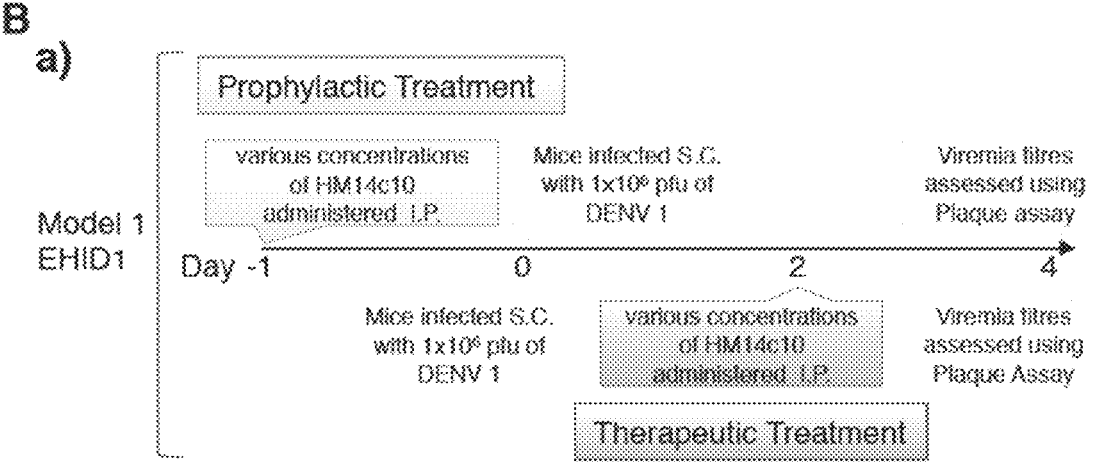
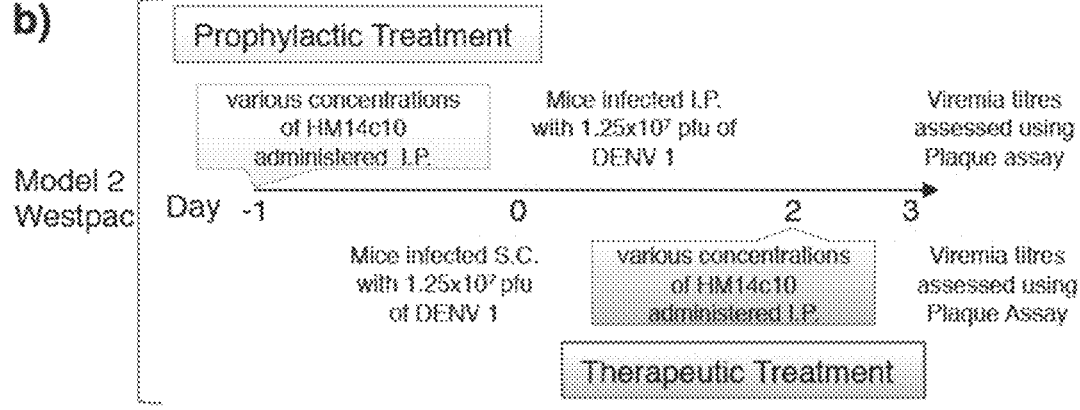
Infectivity and *in vivo* efficacy of labeled DENV1.
Figure 21

Comparison of epitope bound by a West Nile virus antibody CR4354 and dengue 1 specific HM14c10.

Figure 22C

Comparison of epitope bound by a West Nile virus antibody CR4354 and dengue 1 specific HM14c10.

SEQUENCE LISTING

```
<160> NUMBER OF SEQ ID NOS: 42

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asp Gly Arg Thr Ser Leu Asp Trp Phe Leu Leu Arg Pro Gly Gln Phe
        35                  40                  45

Pro Gln Val Lys Ile Ser Glu Leu Ser Arg Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Gly Glu Ala Glu Asp Val Arg Ala Phe Tyr Cys Ile Tyr Gly
                85                  90                  95

Ile Tyr Val Gly Arg Ser Ala Lys Gly Pro Ser Trp Arg Ser Asn
            100                 105                 110

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asp Gly Arg Thr Ser Leu Asp Trp Phe Leu Leu Arg Pro Gly Gln Phe
        35                  40                  45

Pro Gln Val Lys Ile Ser Glu Leu Ser Arg Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Gly Glu Ala Glu Asp Val Arg Ala Phe Tyr Cys Ile Tyr Gly
                85                  90                  95

Ile Tyr Val Gly Arg Ser Ala Lys Gly Pro Ser Trp Arg Ser Asn
            100                 105                 110
```

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Met Thr Gln Ser Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asp Gly Arg Thr Ser Leu Asp Trp Phe Leu Leu Arg Pro Gly Gln Phe
        35                  40                  45

Pro Gln Val Lys Ile Ser Glu Leu Ser Arg Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Gly Glu Ala Glu Asp Val Arg Ala Phe Tyr Cys Ile Tyr Gly
                85                  90                  95

Ile Tyr Val Gly Arg Ser Ala Lys Gly Pro Ser Trp Arg Ser Asn
            100                 105                 110

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Leu Gln Thr Lys Thr Thr Phe Gly Gln Gly Thr Lys Leu Glu Ile Lys
            100                 105                 110

Arg

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Leu Ser Leu Pro Val Thr Pro Gly

```
   1               5                   10                  15
Glu Pro Ala Ser Ile Ser Cys Arg Ser Ser Gln Ser Leu Leu His Thr
                20                  25                  30

Asn Gly Asn Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Leu Gln Thr Lys Thr Thr Phe Gly Gln Gly Thr Lys Leu Glu Ile Lys
                100                 105                 110

Arg
```

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
                20                  25                  30

Asn Gly Asn Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Leu Gln Thr Lys Thr Thr Phe Gly Gln Gly Thr Lys Leu Glu Ile Lys
                100                 105                 110

Arg
```

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Asn Val Tyr Ser Tyr
                20                  25                  30

Leu Gly Trp Tyr Gln His Lys Pro Gly Arg Ser Pro Arg Leu Leu Ile
            35                  40                  45

Phe Gly Val Thr Ser Arg Ala Thr Gly Val Pro Asp Arg Phe Ser Gly
    50                  55                  60
```

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Gly Ser Ala Tyr
                85                  90                  95

Thr Phe Gly Gln Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Asn Val Tyr Ser Tyr
                20                  25                  30

Leu Gly Trp Tyr Gln His Lys Pro Gly Arg Ser Pro Arg Leu Leu Ile
            35                  40                  45

Phe Gly Val Thr Ser Arg Ala Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Gly Ser Ala Tyr
                85                  90                  95

Thr Phe Gly Gln Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Asn Val Tyr Ser Tyr
                20                  25                  30

Leu Gly Trp Tyr Gln His Lys Pro Gly Arg Ser Pro Arg Leu Leu Ile
            35                  40                  45

Phe Gly Val Thr Ser Arg Ala Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Gly Ser Ala Tyr
                85                  90                  95

Thr Phe Gly Gln Gly Thr Lys Val Glu Ile Lys
            100                 105

<210> SEQ ID NO 10
<211> LENGTH: 113
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro His Lys Phe Gly Gln Gly Thr Lys Leu Glu Ile
            100                 105                 110

Lys

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro His Lys Phe Gly Gln Gly Thr Lys Leu Glu Ile
            100                 105                 110

Lys

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu His Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro His Lys Phe Gly Gln Gly Thr Lys Leu Glu Ile
            100                 105                 110

Lys

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Thr
1               5                   10                  15

Ser Val Lys Val Ser Cys Lys Ala Ser Gly Tyr Asn Phe Thr Asp Tyr
            20                  25                  30

Tyr Val His Trp Val Arg Gln Ala Pro Gly Gln Gly Leu Glu Trp Met
        35                  40                  45

Ala Trp Ile Asn Pro Asn Ser Gly Gly Ser Lys Tyr Ala Gln Met Phe
    50                  55                  60

Gln Gly Arg Ile Ser Leu Thr Arg Asp Thr Ser Ile Ser Thr Ala Tyr
65                  70                  75                  80

Leu Glu Leu Phe Ser Leu Thr Ser Asp Asp Thr Ala Val Tyr Tyr Cys
                85                  90                  95

Ala Asp Leu Thr Ala Phe Asp Val Trp Gly Gln Gly Thr Leu Val Thr
            100                 105                 110

Val Ser Ser Gly Thr Thr Val Thr Val Ser Ser
        115                 120

<210> SEQ ID NO 14
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Thr Tyr Tyr Gly Asp Ser Val
    50                  55                  60

Lys Gly Arg Phe Thr Ile Ser Lys Asp Asn Ser Lys Lys Met Val Asn
65                  70                  75                  80

Leu Gln Met Asp Ser Leu Gly Val Glu Asp Thr Ala Phe Tyr Tyr Cys 85                  90                  95

Ala Arg Gly Ile Ala Gly Gly Trp Ala Phe Trp Gly Ile Asp Leu Trp
                100                 105                 110

Gly Gln Gly Thr Leu Val Thr Val Ser Ser
        115                 120

<210> SEQ ID NO 15
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Gly Gly Val Val Arg Pro Gly Lys
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Arg Glu Tyr Gly Ser Gly Ser Tyr Ile Asn Trp Phe Asp Pro Trp
                100                 105                 110

Gly Gln Gly Thr Leu Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Thr
1               5                   10                  15

Ser Val Lys Val Ser Cys Lys Ala Ser Gly Tyr Asn Phe Thr Asp Tyr
            20                  25                  30

Tyr Val His Trp Val Arg Gln Ala Pro Gly Gln Gly Leu Glu Trp Met
        35                  40                  45

Ala Trp Ile Asn Pro Asn Ser Gly Gly Ser Lys Tyr Ala Gln Met Phe
    50                  55                  60

Gln Gly Arg Ile Ser Leu Thr Arg Asp Thr Ser Ile Ser Thr Ala Tyr
65                  70                  75                  80

Leu Glu Leu Phe Ser Leu Thr Ser Asp Asp Thr Ala Val Tyr Tyr Cys
                85                  90                  95

Ala Asp Leu Thr Ala Phe Asp Val Trp Gly Gln Gly Thr Leu Val Thr
                100                 105                 110

Val Ser Ser Gly Thr Thr Val Thr Val Ser Ser
        115                 120

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 17

```
Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Thr Tyr Tyr Gly Asp Ser Val
        50                  55                  60

Lys Gly Arg Phe Thr Ile Ser Lys Asp Asn Ser Lys Lys Met Val Asn
65                  70                  75                  80

Leu Gln Met Asp Ser Leu Gly Val Glu Asp Thr Ala Phe Tyr Tyr Cys
                85                  90                  95

Ala Arg Gly Ile Ala Gly Gly Trp Ala Phe Trp Gly Ile Asp Leu Trp
            100                 105                 110

Gly Gln Gly Thr Leu Val Thr Val Ser Ser
        115                 120
```

<210> SEQ ID NO 18
<211> LENGTH: 122
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

```
Glu Val Gln Leu Val Gln Ser Gly Gly Gly Val Val Arg Pro Gly Lys
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Arg Glu Tyr Gly Ser Gly Ser Tyr Ile Asn Trp Phe Asp Pro Trp
            100                 105                 110

Gly Gln Gly Thr Leu Val Thr Val Ser Ser
        115                 120
```

<210> SEQ ID NO 19
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

Gln Val Gln Leu Val Gln Ser Gly Ala Glu Val Lys Pro Gly Thr
1               5                   10                  15

Ser Val Lys Val Ser Cys Lys Ala Ser Gly Tyr Asn Phe Thr Asp Tyr
            20                  25                  30

Tyr Val His Trp Val Arg Gln Ala Pro Gly Gln Gly Leu Glu Trp Met
        35                  40                  45

Ala Trp Ile Asn Pro Asn Ser Gly Gly Ser Lys Tyr Ala Gln Met Phe
50                  55                  60

Gln Gly Arg Ile Ser Leu Thr Arg Asp Thr Ser Ile Ser Thr Ala Tyr
65                  70                  75                  80

Leu Glu Leu Phe Ser Leu Thr Ser Asp Asp Thr Ala Val Tyr Tyr Cys
                85                  90                  95

Ala Asp Leu Thr Ala Phe Asp Val Trp Gly Gln Gly Thr Leu Val Thr
            100                 105                 110

Val Ser Ser Gly Thr Thr Val Thr Val Ser Ser
            115                 120

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Thr Tyr Tyr Gly Asp Ser Val
50                  55                  60

Lys Gly Arg Phe Thr Ile Ser Lys Asp Asn Ser Lys Lys Met Val Asn
65                  70                  75                  80

Leu Gln Met Asp Ser Leu Gly Val Glu Asp Thr Ala Phe Tyr Tyr Cys
                85                  90                  95

Ala Arg Gly Ile Ala Gly Gly Trp Ala Phe Trp Gly Ile Asp Leu Trp
            100                 105                 110

Gly Gln Gly Thr Leu Val Thr Val Ser Ser
            115                 120

<210> SEQ ID NO 21
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Gly Gly Val Val Arg Pro Gly Lys
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

```
Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Phe Tyr Tyr Cys
                85                  90                  95

Ala Arg Glu Tyr Gly Ser Gly Ser Tyr Ile Asn Trp Phe Asp Pro Trp
            100                 105                 110

Gly Gln Gly Thr Leu Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ala Glu Val Lys Lys Pro Gly Thr
 1               5                  10                  15

Ser Val Lys Val Ser Cys Lys Ala Ser Gly Tyr Asn Phe Thr Asp Tyr
                20                  25                  30

Tyr Val His Trp Val Arg Gln Ala Pro Gly Gln Gly Leu Glu Trp Met
            35                  40                  45

Ala Trp Ile Asn Pro Asn Ser Gly Gly Ser Lys Tyr Ala Gln Met Phe
        50                  55                  60

Gln Gly Arg Ile Ser Leu Thr Arg Asp Thr Ser Ile Ser Thr Ala Tyr
 65                  70                  75                  80

Leu Glu Leu Phe Ser Leu Thr Ser Asp Asp Thr Ala Val Tyr Tyr Cys
                85                  90                  95

Ala Asp Leu Thr Ala Phe Asp Val Trp Gly Gln Gly Thr Leu Val Thr
            100                 105                 110

Val Ser Ser Gly Thr Thr Val Thr Val Ser Ser
        115                 120

<210> SEQ ID NO 23
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Thr Tyr Tyr Gly Asp Ser Val
        50                  55                  60

Lys Gly Arg Phe Thr Ile Ser Lys Asp Asn Ser Lys Lys Met Val Asn
 65                  70                  75                  80

Leu Gln Met Asp Ser Leu Gly Val Glu Asp Thr Ala Phe Tyr Tyr Cys
                85                  90                  95
```

```
Ala Arg Gly Ile Ala Gly Gly Trp Ala Phe Trp Gly Ile Asp Leu Trp
            100                 105                 110

Gly Gln Gly Thr Leu Val Thr Val Ser Ser
        115                 120

<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Gln Ser Gly Gly Gly Val Val Arg Pro Gly Lys
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Arg Glu Tyr Gly Ser Gly Ser Tyr Ile Asn Trp Phe Asp Pro Trp
            100                 105                 110

Gly Gln Gly Thr Leu Val Thr Val Ser Ser
        115                 120

<210> SEQ ID NO 25
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(366)

<400> SEQUENCE: 25 gag gtg cag ctg gtg gag tct ggg gga ggc gtg gtc cag cct ggg agg     48
Glu Val Gln Leu Val Glu Ser Gly Gly Gly Val Val Gln Pro Gly Arg
1               5                   10                  15 tcc ctg aga ctc tcc tgt gca gcg tct gga ttc agc ttc agc agt tat    96
Ser Leu Arg Leu Ser Cys Ala Ala Ser Gly Phe Ser Phe Ser Ser Tyr
            20                  25                  30 ggc atg cac tgg gtc cgc cag gcc cca ggc aag ggg ctg gag tgg gtg   144
Gly Met His Trp Val Arg Gln Ala Pro Gly Lys Gly Leu Glu Trp Val
        35                  40                  45 gca gta ata tgg tat gat gga agt aaa acg tat tat gga gac tcc gtg   192
Ala Val Ile Trp Tyr Asp Gly Ser Lys Thr Tyr Tyr Gly Asp Ser Val
    50                  55                  60 aag ggc cga ttc acc atc tcc aaa gac aat tcc aag aaa atg gtg aat   240
Lys Gly Arg Phe Thr Ile Ser Lys Asp Asn Ser Lys Lys Met Val Asn
65                  70                  75                  80 ctc caa atg gac agc ctg gga gtc gag gac acg gct ttt tat tac tgt   288
Leu Gln Met Asp Ser Leu Gly Val Glu Asp Thr Ala Phe Tyr Tyr Cys
                85                  90                  95
```

```
gca aga ggg ata gcc ggt ggc tgg gcg ttt tgg ggg att gac ctc tgg       336
Ala Arg Gly Ile Ala Gly Gly Trp Ala Phe Trp Gly Ile Asp Leu Trp
            100                 105                 110 ggc cag gga acc ctg gtc acc gtc tcc tca                               366
Gly Gln Gly Thr Leu Val Thr Val Ser Ser
        115                 120

<210> SEQ ID NO 26
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 26 gat gtt gtg atg act cag tct cca ggc acc ctg tct ttg tct cca ggg        48
Asp Val Val Met Thr Gln Ser Pro Gly Thr Leu Ser Leu Ser Pro Gly
1               5                   10                  15 gaa aga gcc acc ctc tcc tgc agg gcc agc cag aat gtt tac agc tac        96
Glu Arg Ala Thr Leu Ser Cys Arg Ala Ser Gln Asn Val Tyr Ser Tyr
            20                  25                  30 tta ggc tgg tac cag cac aaa cct ggc cgg tct ccc agg ctc ctc atc       144
Leu Gly Trp Tyr Gln His Lys Pro Gly Arg Ser Pro Arg Leu Leu Ile
        35                  40                  45 ttt ggt gtc acc agc agg gcc act ggt gtc cca gac agg ttc agt ggc       192
Phe Gly Val Thr Ser Arg Ala Thr Gly Val Pro Asp Arg Phe Ser Gly
    50                  55                  60 agt ggg tct ggg aca gac ttc act ctc acc atc agc aga ctg gag cct       240
Ser Gly Ser Gly Thr Asp Phe Thr Leu Thr Ile Ser Arg Leu Glu Pro
65                  70                  75                  80 gaa gat ttt gcg gtg tac tac tgt cag cag tac gct ggc tca gcg tac       288
Glu Asp Phe Ala Val Tyr Tyr Cys Gln Gln Tyr Ala Gly Ser Ala Tyr
                85                  90                  95 act ttt ggc cag ggg acc aag gtg gag atc aaa cgt                       324
Thr Phe Gly Gln Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Val Val Met Thr Gln Ser Pro Gly Thr Leu Ser Leu Ser Pro Gly
1               5                   10                  15

Glu Arg Ala Thr Leu Ser Cys Arg Ala Ser Gln Asn Val Tyr Ser Tyr
            20                  25                  30

Leu Gly Trp Tyr Gln His Lys Pro Gly Arg Ser Pro Arg Leu Leu Ile
        35                  40                  45

Phe Gly Val Thr Ser Arg Ala Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Gly Ser Ala Tyr
                85                  90                  95
```

Thr Phe Gly Gln Gly Thr Lys Val Glu Ile Lys Arg
            100                 105

<210> SEQ ID NO 28
<211> LENGTH: 495
<212> TYPE: PRT
<213> ORGANISM: Dengue virus

<400> SEQUENCE: 28

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Pro Phe Lys Leu Glu Lys Glu Met Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Val
            340                 345                 350

Thr Ala Asn Pro Ile Val Thr Asp Lys Glu Lys Pro Ile Asn Ile Glu

```
                355                 360                 365
Ala Glu Pro Pro Phe Gly Glu Ser Tyr Ile Val Val Gly Ala Gly Glu
370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Val His Gln Ile Phe Gly Thr Ala Tyr Gly Val Leu Phe
                435                 440                 445

Ser Gly Val Ser Trp Thr Met Lys Ile Gly Ile Gly Ile Leu Leu Thr
                450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 29
<211> LENGTH: 495
<212> TYPE: PRT
<213> ORGANISM: Dengue virus

<400> SEQUENCE: 29

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
                100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Glu Lys Lys Ser Trp Leu Val
            195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240
```

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Gly Ala Gly Glu
370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
            420                 425                 430

Gly Lys Leu Ile His Gln Ile Phe Gly Thr Ala Tyr Gly Val Leu Phe
        435                 440                 445

Ser Gly Val Ser Trp Thr Met Lys Ile Gly Ile Gly Ile Leu Leu Thr
450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 30
<211> LENGTH: 495
<212> TYPE: PRT
<213> ORGANISM: Dengue virus

<400> SEQUENCE: 30

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
            165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
            245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
            325                 330                 335

Phe Leu Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
            405                 410                 415

Asp Thr Ala Trp Asp Phe Gly Ser Ile Gly Gly Val Phe Thr Ser Val
            420                 425                 430

Gly Lys Leu Val His Gln Ile Phe Gly Thr Ala Tyr Gly Val Leu Phe
        435                 440                 445

Ser Gly Val Ser Trp Thr Met Lys Ile Gly Ile Gly Val Leu Leu Thr
450                 455                 460

Trp Leu Gly Leu Asn Ser Arg Ser Thr Ser Leu Ser Met Thr Cys Ile
465                 470                 475                 480

Ala Val Gly Leu Val Thr Leu Tyr Leu Gly Val Met Val Gln Ala
            485                 490                 495

<210> SEQ ID NO 31
<211> LENGTH: 495
<212> TYPE: PRT
<213> ORGANISM: Dengue virus

<400> SEQUENCE: 31

Met Arg Cys Val Gly Ile Gly Asn Arg Asp Phe Val Glu Gly Leu Ser

-continued

```
1               5                   10                  15
Gly Ala Thr Trp Val Asp Val Leu Glu His Gly Ser Cys Val Thr
            20                  25                  30
Thr Met Ala Lys Asp Lys Pro Thr Leu Asp Ile Glu Leu Leu Lys Thr
                35                  40                  45
Glu Val Thr Asn Pro Ala Val Leu Arg Lys Leu Cys Ile Glu Ala Lys
50                  55                  60
Ile Ser Asn Thr Thr Thr Asp Ser Arg Cys Pro Thr Gln Gly Glu Ala
65                  70                  75                  80
Thr Leu Val Glu Glu Gln Asp Ala Asn Phe Val Cys Arg Arg Thr Phe
                85                  90                  95
Val Asp Arg Gly Trp Gly Asn Gly Cys Gly Leu Phe Gly Lys Gly Ser
                100                 105                 110
Leu Ile Thr Cys Ala Lys Phe Lys Cys Val Thr Lys Leu Glu Gly Lys
                115                 120                 125
Ile Val Gln Tyr Glu Asn Leu Lys Tyr Ser Val Ile Val Thr Val His
                130                 135                 140
Thr Gly Asp Gln His Gln Val Gly Asn Glu Thr Thr Glu His Gly Thr
145                 150                 155                 160
Ile Ala Thr Ile Thr Pro Gln Ala Pro Thr Ser Glu Ile Gln Leu Thr
                165                 170                 175
Asp Tyr Gly Ala Leu Thr Leu Asp Cys Ser Pro Arg Thr Gly Leu Asp
                180                 185                 190
Phe Asn Glu Met Val Leu Leu Thr Met Lys Glu Lys Ser Trp Leu Val
                195                 200                 205
His Lys Gln Trp Phe Leu Asp Leu Pro Leu Pro Trp Thr Ser Gly Ala
210                 215                 220
Ser Thr Pro Gln Glu Thr Trp Asn Arg Glu Asp Leu Leu Val Thr Phe
225                 230                 235                 240
Lys Thr Ala His Ala Lys Lys Gln Glu Val Ala Val Leu Gly Ser Gln
                245                 250                 255
Glu Gly Ala Met His Thr Ala Leu Thr Gly Ala Thr Glu Ile Gln Thr
                260                 265                 270
Ser Gly Thr Thr Lys Ile Phe Ala Gly His Leu Lys Cys Arg Leu Lys
                275                 280                 285
Met Asp Lys Leu Thr Leu Lys Gly Met Ser Tyr Val Met Cys Thr Gly
                290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
                325                 330                 335
Phe Ser Thr Gln Asp Glu Lys Gly Val Thr Gln Asn Gly Arg Leu Ile
                340                 345                 350
Thr Ala Asn Pro Ile Val Thr Asp Lys Glu Lys Pro Val Asn Ile Glu
                355                 360                 365
Ala Glu Pro Pro Phe Gly Glu Ser Tyr Ile Val Val Gly Ala Gly Glu
                370                 375                 380
Lys Ala Leu Lys Leu Ser Trp Phe Lys Lys Gly Ser Ser Ile Gly Lys
385                 390                 395                 400
Met Leu Glu Ala Thr Ala Arg Gly Ala Arg Arg Met Ala Ile Leu Gly
                405                 410                 415
Asp Thr Ala Trp Asp Phe Gly Ser Ile Gly Gly Val Phe Thr Ser Val
                420                 425                 430
```

```
Gly Lys Leu Val His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
450                 455                 460

Trp Leu Gly Leu Asn Ser Arg Ser Ala Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 32
<211> LENGTH: 495
<212> TYPE: PRT
<213> ORGANISM: Dengue virus

<400> SEQUENCE: 32

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
```

```
               305                 310                 315                 320
Leu Val Gln Ile Lys Tyr Glu Gly Thr Asp Ala Pro Cys Lys Ile Pro
                    325                 330                 335

Phe Ser Thr Gln Asp Glu Lys Gly Val Thr Gln Asn Gly Arg Leu Ile
                    340                 345                 350

Thr Ala Asn Pro Ile Val Thr Asp Lys Glu Lys Pro Val Asn Ile Glu
                    355                 360                 365

Ala Glu Pro Pro Phe Gly Glu Ser Tyr Ile Val Ile Gly Ala Gly Glu
                370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                    405                 410                 415

Asp Thr Ala Trp Asp Phe Gly Ser Ile Gly Gly Val Phe Thr Ser Val
                    420                 425                 430

Gly Lys Leu Val His Gln Ile Phe Gly Thr Ala Tyr Gly Val Leu Phe
                    435                 440                 445

Ser Gly Val Ser Trp Thr Met Lys Ile Gly Ile Gly Val Leu Leu Thr
                450                 455                 460

Trp Leu Gly Leu Asn Ser Arg Ser Thr Ser Leu Ser Met Thr Cys Ile
465                 470                 475                 480

Ala Val Gly Leu Val Thr Leu Tyr Leu Gly Val Met Val Gln Ala
                    485                 490                 495

<210> SEQ ID NO 33
<211> LENGTH: 396
<212> TYPE: PRT
<213> ORGANISM: Dengue virus

<400> SEQUENCE: 33

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
        50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190
```

Phe Asn Glu Met Val Leu Leu Thr Met Lys Glu Lys Ser Trp Leu Val
            195                 200                 205

His Lys Gln Trp Phe Leu Asp Leu Pro Leu Pro Trp Thr Ser Gly Ala
    210                 215                 220

Ser Thr Pro Gln Glu Thr Trp Asn Arg Glu Asp Leu Leu Val Thr Phe
225                 230                 235                 240

Lys Thr Ala His Ala Lys Lys Gln Glu Val Ala Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Lys Ile Phe Ala Gly His Leu Lys Cys Arg Leu Lys
            275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser
385                 390                 395

<210> SEQ ID NO 34
<211> LENGTH: 396
<212> TYPE: PRT
<213> ORGANISM: Dengue virus

<400> SEQUENCE: 34

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

```
Asp Tyr Gly Ala Leu Thr Leu Asp Cys Ser Pro Arg Thr Gly Leu Asp
                180                 185                 190

Phe Asn Glu Met Val Leu Leu Thr Met Lys Glu Lys Ser Trp Leu Val
            195                 200                 205

His Lys Gln Trp Phe Leu Asp Leu Pro Leu Pro Trp Thr Ser Gly Ala
        210                 215                 220

Ser Thr Pro Gln Glu Thr Trp Asn Arg Glu Asp Leu Leu Val Thr Phe
225                 230                 235                 240

Lys Thr Ala His Ala Lys Lys Gln Glu Val Ala Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Lys Ile Phe Ala Gly His Leu Lys Cys Arg Leu Lys
        275                 280                 285

Met Asp Lys Leu Thr Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
370                 375                 380

Lys Ala Leu Lys Leu Ser Trp Phe Lys Lys Gly Ser
385                 390                 395

<210> SEQ ID NO 35
<211> LENGTH: 396
<212> TYPE: PRT
<213> ORGANISM: Dengue virus

<400> SEQUENCE: 35

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
```

```
              145                 150                 155                 160
        Ile Ala Thr Ile Thr Pro Gln Ala Pro Thr Ser Glu Ile Gln Leu Thr
                            165                 170                 175

Asp Tyr Gly Ala Leu Thr Leu Asp Cys Ser Pro Arg Thr Gly Leu Asp
                        180                 185                 190

Phe Asn Glu Met Val Leu Leu Thr Met Lys Glu Lys Ser Trp Leu Val
                    195                 200                 205

His Lys Gln Trp Phe Leu Asp Leu Pro Leu Pro Trp Thr Ser Gly Ala
                210                 215                 220

Ser Thr Ser Gln Glu Thr Trp Asn Arg Gln Asp Leu Leu Val Thr Phe
        225                 230                 235                 240

Lys Thr Ala His Ala Lys Lys Gln Glu Val Val Val Leu Gly Ser Gln
                        245                 250                 255

Glu Gly Ala Met His Thr Ala Leu Thr Gly Ala Thr Glu Ile Gln Thr
                    260                 265                 270

Ser Gly Thr Thr Thr Ile Phe Ala Gly His Leu Lys Cys Arg Leu Lys
                275                 280                 285

Met Asp Lys Leu Thr Leu Lys Gly Met Ser Tyr Val Met Cys Thr Gly
            290                 295                 300

Pro Phe Lys Leu Glu Lys Glu Met Ala Glu Thr Gln His Gly Thr Val
        305                 310                 315                 320

Leu Val Gln Val Lys Tyr Glu Gly Thr Asp Ala Pro Cys Lys Ile Pro
                        325                 330                 335

Phe Ser Ser Gln Asp Glu Lys Gly Val Thr Gln Asn Gly Arg Leu Val
                    340                 345                 350

Thr Ala Asn Pro Ile Val Thr Asp Lys Glu Lys Pro Ile Asn Ile Glu
                355                 360                 365

Ala Glu Pro Pro Phe Gly Glu Ser Tyr Ile Val Val Gly Ala Gly Glu
            370                 375                 380

Lys Ala Leu Lys Leu Ser Trp Phe Lys Lys Gly Ser
        385                 390                 395

<210> SEQ ID NO 36
        <211> LENGTH: 396
        <212> TYPE: PRT
        <213> ORGANISM: Dengue virus

<400> SEQUENCE: 36

Met Arg Cys Val Gly Ile Gly Asn Arg Asp Phe Val Glu Gly Leu Ser
        1               5                   10                  15

Gly Ala Thr Trp Val Asp Val Val Leu Glu His Gly Ser Cys Val Thr
                        20                  25                  30

Thr Met Ala Lys Asp Lys Pro Thr Leu Asp Ile Glu Leu Leu Lys Thr
                    35                  40                  45

Glu Val Thr Asn Pro Ala Val Leu Arg Lys Leu Cys Ile Glu Ala Lys
                50                  55                  60

Ile Ser Asn Thr Thr Thr Asp Ser Arg Cys Pro Thr Gln Gly Glu Ala
        65                  70                  75                  80

Thr Leu Val Glu Glu Gln Asp Thr Asn Phe Val Cys Arg Arg Thr Phe
                        85                  90                  95

Val Asp Arg Gly Trp Gly Asn Gly Cys Gly Leu Phe Gly Lys Gly Ser
                    100                 105                 110

Leu Ile Thr Cys Ala Lys Phe Lys Cys Val Thr Lys Leu Glu Gly Lys
                115                 120                 125
```

```
Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Glu Lys Lys Ser Trp Leu Val
            195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Val Met Cys Thr Gly
            290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
                355                 360                 365

Ala Glu Pro Pro Phe Gly Glu Ser Tyr Ile Val Gly Ala Gly Glu
                370                 375                 380

Lys Ala Leu Lys Leu Ser Trp Phe Lys Lys Gly Ser
385                 390                 395

<210> SEQ ID NO 37
<211> LENGTH: 396
<212> TYPE: PRT
<213> ORGANISM: Dengue virus

<400> SEQUENCE: 37

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
                100                 105                 110
```

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly Ser
385                 390                 395

<210> SEQ ID NO 38
<211> LENGTH: 396
<212> TYPE: PRT
<213> ORGANISM: Dengue virus

<400> SEQUENCE: 38

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe

```
            85                  90                  95
Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
            130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Thr Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
            195                 200                 205

His Lys Gln Trp Phe Leu Asp Leu Pro Leu Pro Trp Thr Ser Gly Ala
            210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
                275                 280                 285

Met Asp Lys Leu Thr Leu Lys Gly Met Ser Tyr Val Met Cys Thr Gly
            290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Leu Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Ile Gly Ala Gly Glu
            370                 375                 380

Lys Ala Leu Lys Leu Ser Trp Phe Lys Lys Gly Ser
385                 390                 395

<210> SEQ ID NO 39
<211> LENGTH: 394
<212> TYPE: PRT
<213> ORGANISM: Dengue virus

<400> SEQUENCE: 39

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60
```

-continued

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Ser Gln Ala Ser Thr Ala Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Lys Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Thr Ser Gly
            260                 265                 270

Gly Thr Ser Ile Phe Ala Gly His Leu Lys Cys Arg Leu Lys Met Asp
        275                 280                 285

Lys Leu Lys Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Arg Lys Gly Ser
385                 390

<210> SEQ ID NO 40
<211> LENGTH: 396
<212> TYPE: PRT
<213> ORGANISM: Dengue virus

<400> SEQUENCE: 40

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
50 55 60

Leu Thr Asn Thr Thr Thr Asp Ser Arg Cys Pro Thr Gln Gly Glu Pro
65 70 75 80

Ser Leu Asn Glu Glu Gln Asp Lys Arg Phe Val Cys Lys His Ser Met
85 90 95

Val Asp Arg Gly Trp Gly Asn Gly Cys Gly Leu Phe Gly Lys Gly Gly
100 105 110

Ile Val Thr Cys Ala Met Phe Thr Cys Lys Lys Asn Met Lys Gly Lys
115 120 125

Val Val Gln Pro Glu Asn Leu Glu Tyr Thr Ile Val Ile Thr Pro His
130 135 140

Ser Gly Glu Glu His Ala Val Gly Asn Asp Thr Gly Lys His Gly Lys
145 150 155 160

Glu Ile Lys Ile Thr Pro Gln Ser Ser Ile Thr Glu Ala Glu Leu Thr
165 170 175

Gly Tyr Gly Thr Val Thr Met Glu Cys Ser Pro Arg Thr Gly Leu Asp
180 185 190

Phe Asn Glu Met Val Leu Leu Gln Met Glu Asn Lys Ala Trp Leu Val
195 200 205

His Arg Gln Trp Phe Leu Asp Leu Pro Leu Pro Trp Leu Pro Gly Ala
210 215 220

Asp Thr Gln Gly Ser Asn Trp Ile Gln Lys Glu Thr Leu Val Thr Phe
225 230 235 240

Lys Asn Pro His Ala Lys Lys Gln Asp Val Val Val Leu Gly Ser Gln
245 250 255

Glu Gly Ala Met His Thr Ala Leu Thr Gly Ala Thr Glu Ile Gln Met
260 265 270

Ser Ser Gly Asn Leu Leu Phe Thr Gly His Leu Lys Cys Arg Leu Arg
275 280 285

Met Asp Lys Leu Gln Leu Lys Gly Met Ser Tyr Ser Met Cys Thr Gly
290 295 300

Lys Phe Lys Val Val Lys Glu Ile Ala Glu Thr Gln His Gly Thr Ile
305 310 315 320

Val Ile Arg Val Gln Tyr Glu Gly Asp Gly Ser Pro Cys Lys Ile Pro
325 330 335

Phe Glu Ile Met Asp Leu Glu Lys Arg His Val Leu Gly Arg Leu Ile
340 345 350

Thr Val Asn Pro Ile Val Thr Glu Lys Asp Ser Pro Val Asn Ile Glu
355 360 365

Ala Glu Pro Pro Phe Gly Asp Ser Tyr Ile Ile Ile Gly Val Glu Pro
370 375 380

Gly Gln Leu Lys Leu Asn Trp Phe Lys Lys Gly Ser
385 390 395

<210> SEQ ID NO 41
<211> LENGTH: 395
<212> TYPE: PRT
<213> ORGANISM: Dengue virus

<400> SEQUENCE: 41

Met Arg Cys Val Gly Val Gly Asn Arg Asp Phe Val Glu Gly Val Ser
1 5 10 15

Gly Gly Ala Trp Val Asp Leu Val Leu Glu His Gly Gly Cys Val Thr

```
            20                  25                  30
Thr Met Ala Gln Gly Lys Pro Thr Leu Asp Phe Glu Leu Ile Lys Thr
        35                  40                  45
Thr Ala Lys Glu Val Ala Leu Leu Arg Thr Tyr Cys Ile Glu Ala Ser
50                  55                  60
Ile Ser Asn Ile Thr Thr Ala Thr Arg Cys Pro Thr Gln Gly Glu Pro
65                  70                  75                  80
Tyr Leu Lys Glu Glu Gln Asp Gln Gln Tyr Ile Cys Arg Arg Asp Val
                85                  90                  95
Val Asp Arg Gly Trp Gly Asn Gly Cys Gly Leu Phe Gly Lys Gly Gly
            100                 105                 110
Val Val Thr Cys Ala Lys Phe Ser Cys Ser Gly Lys Ile Thr Gly Asn
            115                 120                 125
Leu Val Gln Ile Glu Asn Leu Glu Tyr Thr Val Val Val Thr Val His
            130                 135                 140
Asn Gly Asp Thr His Ala Val Gly Asn Asp Ile Pro Asn His Gly Val
145                 150                 155                 160
Thr Ala Thr Ile Thr Pro Arg Ser Pro Ser Val Glu Val Lys Leu Pro
                165                 170                 175
Asp Tyr Gly Glu Leu Thr Leu Asp Cys Glu Pro Arg Ser Gly Ile Asp
            180                 185                 190
Phe Asn Glu Met Ile Leu Met Lys Met Lys Lys Thr Trp Leu Val
            195                 200                 205
His Lys Gln Trp Phe Leu Asp Leu Pro Leu Pro Trp Ala Ala Gly Ala
            210                 215                 220
Asp Thr Ser Glu Val His Trp Asn Tyr Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Thr Gly Ala Thr Glu Val Asp Ser
            260                 265                 270
Gly Asp Gly Asn His Met Phe Ala Gly His Leu Lys Cys Lys Val Arg
            275                 280                 285
Met Glu Lys Leu Arg Ile Lys Gly Met Ser Tyr Thr Met Cys Ser Gly
            290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Gly Arg Ile Ile Ser
            340                 345                 350
Ser Thr Pro Phe Ala Glu Tyr Thr Asn Ser Val Thr Asn Ile Glu Leu
            355                 360                 365
Glu Pro Pro Phe Gly Asp Ser Tyr Ile Val Ile Gly Val Gly Asp Ser
            370                 375                 380
Ala Leu Thr Leu His Trp Phe Arg Lys Gly Ser
385                 390                 395

<210> SEQ ID NO 42
<211> LENGTH: 402
<212> TYPE: PRT
<213> ORGANISM: West nile virus

<400> SEQUENCE: 42
```

-continued

```
Phe Asn Cys Leu Gly Met Ser Asn Arg Asp Phe Leu Glu Gly Val Ser
1               5                   10                  15
Gly Ala Thr Trp Val Asp Leu Val Leu Glu Gly Asp Ser Cys Val Thr
            20                  25                  30
Ile Met Ser Lys Asp Lys Pro Thr Ile Asp Val Lys Met Met Asn Met
        35                  40                  45
Glu Ala Ala Asn Leu Ala Glu Val Arg Ser Tyr Cys Tyr Leu Ala Thr
50                  55                  60
Val Ser Asp Leu Ser Thr Lys Ala Ala Cys Pro Thr Met Gly Glu Ala
65                  70                  75                  80
His Asn Asp Lys Arg Ala Asp Pro Ala Phe Val Cys Arg Gln Gly Val
                85                  90                  95
Val Asp Arg Gly Trp Gly Asn Gly Cys Gly Leu Phe Gly Lys Gly Ser
            100                 105                 110
Ile Asp Thr Cys Ala Lys Phe Ala Cys Ser Thr Lys Ala Ile Gly Arg
        115                 120                 125
Thr Ile Leu Lys Glu Asn Ile Lys Tyr Glu Val Ala Ile Phe Val His
    130                 135                 140
Gly Pro Thr Thr Val Glu Ser His Gly Asn Tyr Ser Thr Gln Val Gly
145                 150                 155                 160
Ala Thr Gln Ala Gly Arg Leu Ser Ile Thr Pro Ala Ala Pro Ser Tyr
                165                 170                 175
Thr Leu Lys Leu Gly Glu Tyr Gly Glu Val Thr Val Asp Cys Glu Pro
            180                 185                 190
Arg Ser Gly Ile Asp Thr Asn Ala Tyr Tyr Val Met Thr Val Gly Thr
        195                 200                 205
Lys Thr Phe Leu Val His Arg Glu Trp Phe Met Asp Leu Asn Leu Pro
    210                 215                 220
Trp Ser Ser Ala Gly Ser Thr Val Trp Arg Asn Arg Glu Thr Leu Met
225                 230                 235                 240
Glu Phe Glu Glu Pro His Ala Thr Lys Gln Ser Val Ile Ala Leu Gly
                245                 250                 255
Ser Gln Glu Gly Ala Leu His Gln Ala Leu Ala Gly Ala Ile Pro Val
            260                 265                 270
Glu Phe Ser Ser Asn Thr Val Lys Leu Thr Ser Gly His Leu Lys Cys
        275                 280                 285
Arg Val Lys Met Glu Lys Leu Gln Leu Lys Gly Thr Thr Tyr Gly Val
    290                 295                 300
Cys Ser Lys Ala Phe Lys Phe Leu Gly Thr Pro Ala Asp Thr Gly His
305                 310                 315                 320
Gly Thr Val Val Leu Glu Leu Gln Tyr Thr Gly Thr Asp Gly Pro Cys
                325                 330                 335
Lys Val Pro Ile Ser Ser Val Ala Ser Leu Asn Asp Leu Thr Pro Val
            340                 345                 350
Gly Arg Leu Val Thr Val Asn Pro Phe Val Ser Val Ala Thr Ala Asn
        355                 360                 365
Ala Lys Val Leu Ile Glu Leu Glu Pro Pro Phe Gly Asp Ser Tyr Ile
    370                 375                 380
Val Val Gly Arg Gly Glu Gln Gln Ile Asn His His Trp His Lys Ser
385                 390                 395                 400
Gly Ser
```

HUMAN MONOCLONAL ANTIBODY WITH SPECIFICITY FOR DENGUE VIRUS SEROTYPE 1 E PROTEIN AND USES THEREOF

CROSS REFERENCE TO RELATED APPLICATIONS

This application is the 35 U.S.C. 371 national stage entry of PCT/SG2011/000436 and claims priority to U.S. Provisional Patent Application No. 61/423,085, filed Dec. 14, 2010, the disclosure of which is hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 19972_US_PCT_Sequence_Listing.txt, created on Feb. 29, 2012, 90,112 bytes, machine format IBM-PC, MS-Windows operating system, is hereby incorporated by reference in its entirety for all purposes.

FIELD

The invention relates to human neutralizing monoclonal antibodies to Dengue virus, in particular, serotype 1. The invention further relates to compositions and methods for the treatment or prevention of infection by Dengue virus in a vertebrate subject. Methods are provided for administering antibodies to the vertebrate subject in an amount effective to reduce, eliminate, or prevent relapse from infection.

BACKGROUND

Dengue is the most significant mosquito-borne viral disease affecting humans. At present close to 2.5 billion people living in more than 100 dengue endemic countries in the tropical/sub-tropical belt are considered to be at risk of dengue infection. The urban dwelling mosquito species, Aedes aegypti is the principal transmitter of the virus to humans. Infection with dengue virus can result in a spectrum of clinical manifestations ranging from asymptomatic infection through dengue fever (DF), an acute febrile disease, to dengue haemorrhagic fever (DHF) and dengue shock syndrome (DSS) which are severe, life-threatening complications typified by vascular leakage. Current treatment is limited to the use of analgesics to alleviate the symptoms and there are no vaccines available. Dengue diseases affect 50 million people yearly, with frequent and recurrent epidemics. The 1990's saw a return of dengue diseases in various areas of the world despite stringent mosquito controls, peaking with the largest ever outbreak in 2005 in Singapore. Over 80% of the reported cases were young adults with an associated impact on their ability to work plus significant healthcare costs for their treatment. Hence, alternatives to dengue vaccines, such as passive antibody therapies and/or antivirals are needed urgently to help control dengue associated diseases in the immediate term. These proposed therapeutics have the potential to help large numbers of infected individuals even if only applied to individuals at risk of developing the severe forms of disease (around 10% of the total). With the increasing prevalence of dengue in developed nations such as the Southern United States plus Australia, and the absence of a vaccine, such an antibody would provide a useful medication. The present invention provides fully human monoclonal antibodies to satisfy these and other needs.

SUMMARY

Described herein are compositions and methods for the treatment or prevention of Dengue virus infection in a vertebrate subject.

In particular, disclosed herein is an example of the generation of fully human neutralizing monoclonal antibodies from patients newly recovered from infection with Dengue serotype 1. The antibody exhibits both prophylactic and therapeutic activity in blocking Dengue serotype 1 infection in vitro and in vivo and can form the basis of a new medication. The invention utilizes a method for preparing immortalized memory B cells from convalescent patients by purifying their CD22 positive cells from a blood sample taken 60 days after the patient has recovered from infection. The purified B cells are then immortalized, by employing Epstein Barr Virus (EBV) infection. This method generates a panel of immortalized memory B cell lines capable of producing fully human antibodies which can be screened for specificity for Dengue virus. These B cell lines can then be used as an enriched source of immunoglobulin templates for the identification and cloning of recombinant monoclonal antibodies with neutralizing activity for Dengue virus in vitro and in vivo. As disclosed herein, we describe the isolation, screening, cloning and in vitro/in vivo characterization of the first fully human monoclonal antibody specific for Dengue Virus serotype 1.

In one aspect, the present invention provides an isolated antibody or fragment thereof that binds to a Dengue virus serotype 1 envelope protein or fragment thereof, wherein the antibody is a human antibody with neutralizing activity.

In various embodiments of this aspect, the antibody or fragment thereof can be (a) a whole immunoglobulin molecule; (b) an scFv; (c) a Fab fragment; (d) an F(ab')2; or (e) a disulfide linked Fv.

In other embodiments, the antibody or fragment thereof can comprise a heavy chain immunoglobulin constant domain selected from the group consisting of: (a) a human IgM constant domain; (b) a human IgG1 constant domain; (c) a human IgG2 constant domain; (d) a human IgG3 constant domain; (e) a human IgG4 constant domain; or (f) a human IgA1/2 constant domain.

In yet other embodiments, the antibody or fragment thereof can comprise a light chain immunoglobulin constant domain which can be: (a) a human Ig kappa constant domain; or (b) a human Ig lambda constant domain.

In additional embodiments, the antibody or fragment thereof comprises a heavy chain comprising at least one CDR selected from the group of CDR sequences shown in FIG. 4(B).

In further embodiments, the antibody or fragment thereof comprises a light chain comprising at least one CDR selected from the group of CDR sequences shown in FIG. 4(B).

In other embodiments, the antibody or fragment thereof comprises a heavy chain comprising three CDR sequences as shown in FIG. 4(B).

In other embodiments, the antibody or fragment thereof comprises a light chain comprising three CDR sequences as shown in FIG. 4(B).

In further embodiments, the antibody or fragment thereof comprises a heavy chain framework of IGHV1-2*02 and at least one of the CDR sequences as shown in FIG. 4(B).

In yet further embodiments, the antibody or fragment thereof comprises a light chain framework of IGKV3-20*01 and at least one of the CDR sequences as shown in FIG. 4(B).

In one embodiment, the antibody comprises the heavy chain sequence shown in FIG. 4(B).

In another embodiment, the antibody comprises the light chain sequence shown in FIG. 4(B).

In yet another embodiment, the antibody is 14c10, clone 8.

In some embodiments, the antibody or fragment thereof binds to an antigen with an affinity constant ($K_D$) of less than $1 \times 10^{-8}$ M.

In other embodiments, the antibody or fragment thereof binds to an antigen with an affinity constant ($K_D$) of less than $1 \times 10^{-9}$ M.

In further embodiments, the antibody or fragment thereof is derived from a B cell of a patient who has recovered from Dengue virus infection.

In further embodiments, the antibody or fragment thereof binds across two envelope proteins in a virus. In some embodiments, the binding across two envelope proteins comprises binding to DI and the hinge between DI and II on one E protein and DIII of a neighboring E protein.

In another aspect, the present invention provides an antibody or fragment thereof that binds to a Dengue virus having the binding specificity of 14c10, clone 8.

In a further aspect, the present invention provides a pharmaceutical composition comprising the antibody or fragment thereof according to any one of the relevant aspects and embodiments above and a pharmaceutically acceptable carrier effective to reduce or prevent. Dengue virus infection in a subject. In some embodiments, the pharmaceutical composition can further comprise a second agent, for example, an antiviral drug or an analgesic drug.

In a further aspect, the present invention provides a method of passive immunization comprising administration to a subject an effective amount of the antibody or fragment thereof according to any one of the relevant aspects and embodiments above.

In an additional aspect, the present invention provides a method of treatment of Dengue virus infection comprising administration to a subject in need thereof an amount of antibody or fragment thereof according to any one of the relevant aspects and embodiments above, effective to reduce or prevent the disease.

In some embodiments, the antibody is administered intravenously (IV), subcutaneously (SC), intramuscularly (IM), transdermally, or orally.

In other embodiments, the antibody is administered in an amount in the range of 1 to 100 milligrams per kilogram of the subject's body weight.

Such administration can further comprise administration of a second agent, which can, for example, be an antiviral drug or an analgesic drug.

In another aspect, the present invention provides a method of generating a neutralizing antibody against a Dengue virus by: (a) identifying an individual who has recently recovered from Dengue virus infection; (b) obtaining B-cells from the individual; (c) immortalizing the B-cells from (b); and (d) assaying the immortalized B-cells from (c) for Dengue virus neutralization.

In embodiments of this aspect, the B cells are CD 22+. In further embodiments, the B cells are immortalized with EBV.

In other aspects, the present invention provides an isolated nucleic acid encoding the antibody or fragment thereof according to any one of the relevant aspects and embodiments above. Such isolated nucleic acids can be contained in an expression vector. Such expression vectors can be contained within a host cell, such as a bacterial, eukaryotic, or mammalian cell.

BRIEF DESCRIPTION OF THE DRAWINGS

FIG. 1: Flowchart of the process of antibody screening, expression and characterization. CD22+ B cells from Dengue infected patients admitted to National University Hospital (NUH) were isolated. These B cells were immortalized with EBV in the presence of a polyclonal B cell activator (2.5 µg/ml CpG sequences, IL2 and IL4) which were added to enhance the efficiency of immortalization. B cells were plated at 30 cells/well in 96 wells round bottom wells with $1 \times 10^5$ allogenic, irradiated PBMCs obtained from buffy coats. After two weeks, supernatants from these clones were screened by ELISA, PRNT and CPE for binding/neutralizing activity. mRNA of the positive B cell lines was extracted and the heavy and light chains sequences of the antibody cloned into an in-house pCMV vector and transfected into Freestyle® 293F cells to produce high concentrations of recombinant antibodies. The recombinant antibodies with the desired specificity were identified and further characterized.

FIG. 2: Screening of supernatants from immortalized B cell lines with CPE and PRNT for Dengue neutralizing activity. (A) BHK-21 cells were challenged with DV in the presence of supernatants derived from EBV immortalized B-cell lines. (2000 cell lines per patient were screened using this approach). The cytopathic effect was assessed by staining the remaining intact cells with crystal violet elution with acetic acid and determination of the absorbance at 595 nm. The assay endpoint was defined as a 50% cytopathic effect and the viral concentration was optimized. Test supernatants were screened initially at a dilution of 1 in 4. Top 10% of clones were re-tested by PRNT. (B) Generation of human B lymphocyte cell line secreting neutralising human antibodies against Dengue. BHK cells at 80% confluency were infected with Dengue virus for 3 days. Viral plaques were visualised using crystal violet dye (Sigma-Aldrich, Singapore) that binds to viable cells. Supernatants from B cell clones (derived from a convalescent Dengue 1 infected individual) were tested for neutralising activity. Dengue 1 (50 pfu) was incubated with cell culture supernatants (diluted ¼) for 1 hour prior to addition to BHK cells. Cell line 14c10 was found to secrete antibodies that significantly reduced plaque numbers.

FIG. 3: Antibody templates expressed by B cell line 14C10 and the associated CDR amino acid sequences. (A) Plasmid map demonstrating restriction enzyme sites and cloning heavy and light chains inserts for generation of a recombinant human IgG1 antibody using identified templates from 14c10. (B) All the identified and cloned Heavy and light chain sequences of 14c10 with their CDR regions (CDR 1, CDR 2 and CDR 3 respectively) plus 12 permutations of Heavy and Light Chain combinations to make different recombinant antibodies (SEQ ID NOS:1-24).

FIG. 4: Antibody template 14c10.8 encodes a recombinant antibody with binding activity for dengue serotype 1. (A) Sandwiched ELISA employed to test all recombinantly expressed antibodies derived from the B cell line 14c10 expressed and purified from supernatabnts of 293F. Template number 8 clearly gives a positive signal for dengue virus serotype 1. (B) Full nucleotide and amino acid sequence of 14c10.8 Heavy (SEQ ID NOS:25 and 20, respectively) and Light (SEQ ID NOS:26 and 27, respectively) Chains with CDR regions highlighted.

FIG. 5: Serotype specificity of recombinant 14c10.8 antibody with PRNT and ELISA. (A) Sandwiched ELISA showing specificity of recombinant IgG1 14c10 antibody against live whole dengue virus serotype 1. No observable binding activity for Dengue serotypes 2, 3 or 4. (B) PRNT data showing specificity of recombinant 14c10.8 antibody against Westpac 74 Dengue virus serotype 1. No significant neutralizing activity was detected for Dengue serotype 2, 3 or 4. (C) Raw data of PRNT showing serotype specificity of 14c10.8 for Dengue virus serotype 1.

FIG. 6: 14c10.8 exhibits homotypic antibody dependent enhancement (ADE) but no heterotypic antibody dependent enhancement for in vitro dengue infection. Serially diluted 14c10.8 antibody was incubated with an equal volume of virus (MOI of 1) for 1 hr at 37° C. then transferred to the human myelomonocytic cell line K562 (the cell line usually employed for ADE assays) and incubated at 37° C. for 4 days. Supernatants were then harvested from the infected K562 cells and the resulting viral titre assessed by PRNT. ADE is defined as increased viral titres compared to controls where no antibody is added (dotted blue line). Data demonstrated presence of ADE in dengue virus serotype 1 but not in serotype 2, 3 and 4. This observation suggests that 14c10.8 should be a safe antibody to give to dengue 1 infected patients provided that it's given at neutralizing rather than enhancing concentrations.

FIG. 7: Conversion of 14c10.8 to different human IgG sub-classes has an impact on its homotypic enhancement activity. We converted 14c10 from a human IgG1 to a human IgG3 and human IgG4 using the constructs outlined. These were expressed as recombinant antibodies in 293F cells then purified on Protein-A sepharose columns for further testing. We testing for homotypic enhancement using the K562 cell lines as described in FIG. 6. IgG3 exhibits maximal enhancing activity whilst IgG1 is intermediate and IgG4 has the lowest levels of enhancing activity.

FIG. 8: 14c10.8 is specific for Dengue virus E-protein. (i) Cells were infected with DV for two days. Upon which, cells were lysed and $S^{32}$ methionine was added to the mixture of the virus to incorporate the radioactive compound. Antibody was added to the mixture followed by the addition of Protein A-agarose beads were then added and incubated for 1 hr at 4° C. After washing, proteins were eluted with non-reducing loading buffer and run on a 15% SDS-polyacrylamide gel followed by silver staining according to the manufacture protocol (SilverQuest staining kit, Invitrogen). A 56 Kd band corresponds to E protein of Dengue virus. (ii) Purified whole dengue virus (denatured and non-denatured) was loaded onto non-denaturing gel and transferred to a membrane to be blotted with 14C10 antibody. Results showed that 14C10 has weak binding to a linear epitope on dengue E protein.

FIG. 9: Neutralization activity of recombinant 14c10 antibody against various dengue serotype 1 genotypes. Increasing concentrations of antibody were added to 50 plaque-forming units (p.f.u.) of various genotypes of Dengue virus serotype 1 (viral genotype name is provided in parenthesis) and incubated at 37° C. for 1 hr. 100 µl of mixture was added to a monolayer of BHK-21 cells in a 24 well plate and incubated for 1 hr at 37° C. Supernatant was removed and 1 ml of 2% (w/v) carboxyl methyl cellulose in RPMI plus 2% FBS was layered onto the infected cells. After further incubation at 37° C. for 4 days, the wells were stained with 0.5% (w/v) crystal violet dissolved in 25% (v/v) formaldehyde to visualize the plaques. EU448410=SEQ ID NO:28; DVU88535=SEQ ID NO:29; EU081234=SEQ ID NO:30; AF425619=SEQ ID NO:31; GQ357687=SEQ ID NO:32.

FIG. 10: 14c10 exhibits both prophylactic and therapeutic activity in vivo: (A) Prophylactic activity of 14c10.8 was observed by injecting AG129 (n=6) mice with various concentrations of antibody 24 hours prior to infection with dengue serotype 1. A single therapeutic dose of 250 µg/mouse of antibody was given to a single cohort (n=6) 24 hours after dengue virus infection. The resulting viremia was quantified in the blood serum of infected mice by PRNT 4 days post infection. (B) 14c10.8 exhibits prophylactic activity at concentrations of 1-5 µg/mouse. At lower concentrations of antibody there is some evidence of enhanced infection.

FIG. 19: Fitting of the homology model of HM14c10 variable region into HM14c10:DENV1 cryoEM density map. (A) The densities corresponding to the individual chains (a and b) of the antibody variable region are circled from the cryoEM map. The contact residues of the fitted E protein are indicated with cyan spheres. E-DI, E-DII and E-DIII are colored in red, yellow and blue, respectively. (B) The homology model light and heavy chains were fitted separately into the variable region of the Fab cryoEM densities. [a] For designation of Fab position see FIG. 12. [b] For designation of Fab density see (A). [c] The fits of the homology model into the HM14c10:DENV1 cryoEM map (set at a contour level of 3σ) were optimized by using the fit-in-map function in Chimera (35). (C) The fitted HM variable region homology model (green) showing the CDRs in magenta. The fit shown has light chain in Fab density a, and heavy chain in Fab density b.

FIG. 20: HM14c10 epitope on dengue serotype 1 (genotype PVP159) and comparison of the epitope with (A) other DENV1 genotypes (SEQ ID NOS:33-38) and (B) dengue serotypes and West Nile virus (WNV) (SEQ ID NOS:39-42). Common amino acid residues between the epitopes recognized by Fab HM14c10(I) and Fab HM14c10(II) in an asymmetric unit are colored in green. Residues that are uniquely recognized by Fab HM14c10(I) or Fab HM14c10(II) are colored in purple and cyan, respectively. The amino acid sequences of the epitopes recognized by Fab HM14c10 are conserved within DENV1 genotypes, but not across dengue serotypes or West Nile virus. This is consistent with the observation that Fab HM14c10 binds to most dengue 1 genotypes, but does not cross-react with other dengue serotypes or flaviviruses with shaded antibody footprints (a) at position X1 and II or (b) position X2 and I.

FIG. 21: Infectivity and in vivo efficacy of labeled DENV1. (A) Live DENV labelling was conducted as previously described (22). The infectivity and viability of labeled virus was tested by plaque assay through titration on BHK cells. (B) The in vivo efficacy of HM14c10 was tested in two in vivo models employing different strains/concentrations of DENV1 virus plus different modes of viral delivery. A schematic of both of these models is shown. (a) In model 1, $1\times10^6$ pfu of EHID1 strain is injected sub-cutaneously (S.C.) and the serum viremia monitored by plaque assay 4 days later. Prophylaxes are given 24 h before DENV1 infection and therapeutic applications at day plus 2 post infection. (b) A second more aggressive DENV1 infection model was also employed. Mice were injected intraperitoneally with $1.25\times10^7$ pfu of the Westpac strain of DENV1. Virus infection plus prophylactic and therapeutic treatments were administered via intraperitoneal (I.P.) injection at the same time points as model 1. In this model plasma viremia peaks at day +3 post infection and this is where the effects of the administered antibody on serum viremia is measured. Controls in both groups were given an equal volume of sterile saline.

DETAILED DESCRIPTION

Figure 11:
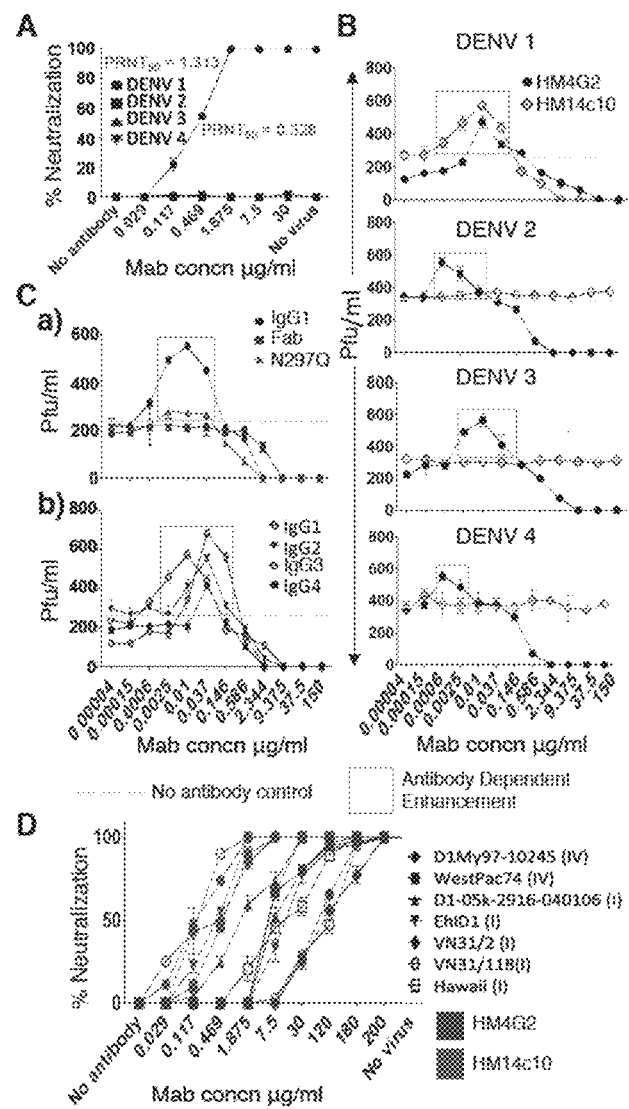
FIG. 11: HM14c10 is a human antibody specific for DENV1. (A) HM14c10 exhibits neutralization activity specific for DENV1 with 50% and 90% PRNT values of 0.328 µg/ml and 1.313 µg/ml, respectively. (B) HM14c10 induces homotypic ADE for DENV1 at sub-neutralizing concentrations but no heterotypic ADE for DENV2, DENV3 or DENV4. HM4G2 induces ADE activity for all 4 serotypes (C) (a) The Fab fragment or mutation (N297Q) of the IgG1 Fc region of HM significantly reduced homotypic ADE. (b) Different subclasses of human IgG (HM14c10) mediate differential levels of homotypic ADE. (D) HM14c10 is highly neutralizing to multiple DENV1 genotypes compared to HM4G2. The genotypes are indicated in brackets beside the virus designation. Error bars represent standard deviations of triplicate samples, and all experiments were conducted at least three times.

The present invention generally relates to compositions and methods for the prevention or treatment of Dengue virus infection in a vertebrate subject. In particular, we have isolated CD22+ B cells from Dengue infected patients admitted to the Infectious disease division of National University Hospital (NUH). These B cells were immortalized as polyclonal cell lines with EBV in vitro. The polyclonal B cell activator (CpG sequences) was added to enhance the efficiency of B cells immortalization along with the human B cell growth factors, Interleukin 2 and Interleukin 4 (1000 U/ml of each). Human B cell lines were made in 96 wells round bottom wells. After two weeks, supernatants from these clones were screened by Enzyme Linked Immunosorbent Assay (ELISA), Plaque reduction neutralization test (PRNT) and Cytopathic Effect assay (CPE) to analyze binding/neutralizing activity for dengue virus. B cell lines producing positive antibodies were used as a source of mRNA for antibody heavy and light chains gene amplification. The heavy and light chains sequences of the antibody were cloned into an in-house pCMV vector and transfected into Freestyle® 293F cells to produce high concentrations of recombinant antibody. Using this methodology, we have cloned and expressed a recombinant antibody that is exquisitely dengue serotype 1 specific and has broad specificity for various Dengue serotype 1 genotypes. This antibody does not bind to other viruses in the *Flavivirus* genus and, as such, exhibits little or no enhancement of infection of macrophages to other *flaviviruses* beyond those expected for dengue serotype 1. In vivo experiments have shown remarkable prophylactic and therapeutic efficacy in a mouse model of dengue infection. As such, this antibody represents the best available candidate therapeutic for dengue 1 infection in existence.

DEFINITIONS

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

"Vertebrate," "mammal," "subject," "mammalian subject," or "patient" are used interchangeably and refer to mammals such as human patients and non-human primates, as well as experimental animals such as rabbits, rats, and mice, cows, horses, goats, and other animals. Animals include all vertebrates, e.g., mammals and non-mammals, such as mice, sheep, dogs, cows, avian species, ducks, geese, pigs, chickens, amphibians, and reptiles.

"Treating" or "treatment" refers generally to either (i) the prevention of infection or reinfection, e.g., prophylaxis, or (ii) the reduction or elimination of symptoms of a disease of interest, e.g., therapy. Treating a subject with the compositions of the invention can prevent or reduce the risk of infection from Dengue virus, particularly serotype 1. Treatment can be prophylactic (to prevent or delay the onset of the disease, or to prevent the manifestation of clinical or subclinical symptoms thereof) or therapeutic suppression or alleviation of symptoms after the manifestation of the disease.

"Preventing" or "prevention" refers to prophylactic administration with compositions of the invention.

"Therapeutically-effective amount" or "an amount effective to reduce or eliminate infection" or "an effective amount" refers to an amount of an antibody composition that is sufficient to prevent Dengue viral infection or to alleviate (e.g., mitigate, decrease, reduce) at least one of the symptoms associated with such an infection. It is not necessary that the administration of the composition eliminate the symptoms of Dengue infection, as long as the benefits of administration of the composition outweigh the detriments. Likewise, the terms "treat" and "treating" in reference to Dengue infection, as used herein, are not intended to mean that the subject is necessarily cured of infection or that all clinical signs thereof are eliminated, only that some alleviation or improvement in the condition of the subject is effected by administration of the composition.

"Passive immunity" refers generally to the transfer of active humoral immunity in the form of pre-made antibodies from one individual to another. Thus, passive immunity is a form of short-term immunization that can be achieved by the transfer of antibodies, which can be administered in several possible forms, for example, as human or animal blood plasma or serum, as pooled animal or human immunoglobulin for intravenous (IVIG) or intramuscular (IG) use, as high-titer animal or human IVIG or IG from immunized subjects or from donors recovering from a disease, and as monoclonal antibodies. Passive transfer can be used prophylactically for the prevention of disease onset, as well as, in the treatment of several types of acute infection. Typically, immunity derived from passive immunization lasts for only a short period of time, and provides immediate protection, but the body does not develop memory, therefore the patient is at risk of being infected by the same pathogen later.

Antibodies

As used herein, the term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term, including IgA, IgD, IgE, IgG, and IgM.

As used herein, the term "antibody fragment" refers specifically to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments.

An intact "antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

As used herein, the term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments and can be prepared by recombinant techniques or enzymatic or chemical cleavage of intact antibodies.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

As used herein, the term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one aspect, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

As used herein, the term "humanized antibody," refers to at least one antibody molecule in which the amino acid sequence in the non-antigen binding regions and/or the antigen-binding regions has been altered so that the antibody more closely resembles a human antibody, and still retains its original binding ability.

In addition, techniques developed for the production of "chimeric antibodies" (Morrison, et al., Proc Natl Acad Sci, 81:6851-6855 (1984), incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

In addition, techniques have been developed for the production of humanized antibodies (see, e.g., U.S. Pat. No. 5,585,089 and U.S. Pat. No. 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

Antibody Assays

A number of screening assays are known in the art for assaying antibodies of interest to confirm their specificity and affinity and to determine whether those antibodies cross-react with other proteins.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The affinity binding constant ($K_{aff}$) can be determined using the following formula:

$$K_{aff} = \frac{(n-1)}{2(n[mAb']_t - [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg']_t$) (Beatty et al., J Imm Meth, 100:173-179 (1987)).

The term "high affinity" for an antibody refers to an equilibrium association constant ($K_{aff}$) of at least about $1 \times 10^7$ liters/mole, or at least about $1 \times 10^8$ liters/mole, or at least about $1 \times 10^9$ liters/mole, or at least about $1 \times 10^{10}$ liters/mole, or at least about $1 \times 10^{11}$ liters/mole, or at least about $1 \times 10^{12}$ liters/mole, or at least about $1 \times 10^{13}$ liters/mole, or at least about $1 \times 10^{14}$ liters/mole or greater. "High affinity" binding can vary for antibody isotypes. $K_D$, the equilibrium dissociation constant, is a term that is also used to describe antibody affinity and is the inverse of $K_{aff}$.

$K_D$, the equilibrium dissociation constant, is a term that is also used to describe antibody affinity and is the inverse of $K_{aff}$. If $K_D$ is used, the term "high affinity" for an antibody refers to an equilibrium dissociation constant ($K_D$) of less than about $1 \times 10^{-7}$ mole/liters, or less than about $1 \times 10^{-8}$ mole/liters, or less than about $1 \times 10^{-9}$ mole/liters, or less than about $1 \times 10^{-10}$ mole/liters, or less than about $1 \times 10^{-11}$ mole/liters, or less than about $1 \times 10^{-12}$ mole/liters, or less than about $1 \times 10^{13}$ mole/liters, or less than about $1 \times 10^{-14}$ mole/liters or lower.

The production of antibodies according to the present disclosure provides for antibodies with the characteristics of those produced in the course of a physiological human immune response, i.e. antibody specificities that can only be selected by the human immune system. In the present case, this includes a response to the human pathogen Dengue virus, serotype 1. In some embodiments, antibodies of the present disclosure possess the characteristics of those produced in the course of a response to infection by Dengue virus. These antibodies can be used as prophylactic or therapeutic agents upon appropriate formulation.

In relation to a particular pathogen, a "neutralizing antibody", "broadly neutralizing antibody", or "neutralizing monoclonal antibody", all of which are used interchangeably herein, is one that can neutralize the ability of that pathogen to initiate and/or perpetuate an infection in a host. In some embodiments, monoclonal antibodies produced in accordance with the present disclosure have neutralizing activity, where the antibody can neutralize at a concentration of $10^{-9}$M or lower (e.g. $10^{-10}$ M, $10^{-11}$M, $10^{-12}$M or lower).

The immunoglobulin molecules of the present invention can be of any type (e.g., IgG, IgE, IgM, IgD, IgA and IgY), class (e.g., IgG1, IgG2, IgG3, IgG4, IgA1 and IgA2), or subclass of immunoglobulin molecule. In some embodiments, the antibodies are antigen-binding antibody fragments (e.g., human) and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, CH1, CH2, and CH3 domains. Also included in the present disclosure are antigen-binding fragments comprising any combination of variable region(s) with a hinge region, CH1, CH2, and CH3 domains.

B Cell Isolation

As used herein, the terms "B cell", "B memory cell", "B lymphocyte", "B memory lymphocyte", "memory cells", "memory B cell", and variants thereof are used interchangeably and refer to B cells of the humoral immune response. As understood in the art, B cells are lymphocytes that play a role in the humoral immune response (as opposed to the cell-mediated immune response, which is governed by T cells). At least one function of B cells is to make antibodies against antigens, perform the role of Antigen Presenting Cells (APCs) and eventually develop into memory B cells after activation by antigen interaction. B cells are a component of the adaptive immune system.

The phrase "primary B cell" can refer in some embodiments to a B cell taken directly from a living organism (e.g., a human). In some embodiments, a primary B cell can be cultured in a primary cell culture. A primary B cell can be derived, obtained or collected from a subject in any manner known to those of skill in the art. In some embodiments, a primary B cell is obtained from a subject infected with or possessing an antigen of interest.

The methods of the present disclosure can be applied for the identification of monoclonal antibodies expressed by human B cells selected from donors, such as patients exposed to an infective agent, e.g., Dengue virus. Thus, the donor can be naive, vaccinated, affected by one or more diseases or infections, already exposed and/or resistant to specific therapeutic treatments, presenting a specific clinical index or status, inadvertently exposed to a pathogen, etc.

A donor's sera can be used as such for an initial determination of their seropositivity to an antigen, since the specificity and long-term maintenance of the adaptive immune responses (even years after the last exposure to this antigen) may allow a qualitative determination that is sufficient for selecting donors. The nature and sensitivity of the screening assay used is critical in identifying the most suitable donor and, preferably, the assay used to screen donor serum should be the same as that used to screen supernatants from immortalized antibody-secreting B cells and designed to detect an antibody with the desired functional activity (i.e., neutralization activity).

The choice of the tissue or the organ from which the cells are purified may be dictated by the availability of appropriate cells in sufficient amount. Cells can be obtained from fresh or frozen samples and/or from samples obtained from a number of individuals that have been pooled to provide enough starting material.

A preliminary screen can be done on a panel of candidate donors, using samples containing antibody-secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be pre-screened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays).

Examples in the art include, for example, the use of ELISPOT for characterizing the immune response in vaccinated donors (Crotty S et al., 2004), the use of antigen microarrays as diagnostic tools for newly infected patients (Mezzasoma L et al., 2002), and other technologies for measuring antigen-specific immune responses (Kern F et al., 2005).

This preliminary qualitative analysis of antibody response to the therapeutic target should allow the identification of donors having B cells expressing higher antibody titers directed to the desired purified antigen (e.g. a specific recombinant viral protein), a mixture of related antigens (e.g. obtained from partially purified viral preparation), or a bioassay (e.g. neutralization of viral infectivity).

Once one or more donors are selected, the source of B cells can be spleen, blood, lymph nodes, bone marrow, tumor infiltrating lymphocytes, lymphocytes from sites of chronic infection/inflammation. However, peripheral blood is usually easier to obtain from donors, to store, and to monitor for the serological response against an antigen over a defined period of time.

For example, starting from 5-50 ml of peripheral blood, approximately 10-100 million of PBMCs (peripheral blood mononuclear cells) can be purified, a number of cells that would allow a sufficiently large population of antibody-secreting cells to be screened after being immortalized using the methods disclosed herein.

After the isolation of PBMCs from biological samples, a specific selection of antibody-secreting cells can be performed, using methods known in the art, on the basis of the expression of cell surface markers on their surface and, if appropriate, of other proteins, as well as the proliferation activity, the metabolic and/or morphological status of the cells.

In particular, various technologies for the purification of antibody-secreting cells from human samples make use of different means and conditions for positive or negative selection. These cells can be efficiently selected by physically separating those expressing cell surface markers specific for cells that express and secrete antibodies (e.g. human B cells). Specific protocols can be found in the art (see, e.g., Callard R and Kotowicz K "Human B-cell responses to cytokines" in Cytokine Cell Biology: A practical Approach. Balkwill F. (ed.) Oxford University Press, 2000, pg. 17-31).

The selection can be performed using antibodies that bind specifically to one of these cell surface proteins and that can be linked to solid supports (e.g. microbeads or plastic plates) or labeled with a fluorochrome that can be detected using fluorescence-activated cell sorters (FACS). For example, human B cells have been selected on the basis of their affinity for supports (such as microbeads) binding CD19, CD27, and/or CD22 microbeads, or for the lack of binding affinity for antibodies specific for certain isotypes prior to EBV immortalization (Li H et al., 1995, Bernasconi N et al., 2003; Traggiai E et al., 2004).

As shown herein, CD22, which is a B-cell restricted transmembrane protein that controls signal transduction pathways related to antigen recognition and B cell activation (Nitschke L, 2005), can be used for the initial B cell selection. Since the CD22 positive population contains cells that express antibodies having different isotypes and specificities, other cell surface markers can also be used for selecting the cells.

Alternatively or additionally, a specific enrichment of antibody-secreting cells can be obtained by applying a CD27-based selection in addition to the CD22-based selection. CD27 is known to be a marker for human B cells that have somatically mutated variable region genes (Borst J et al., 2005). Additional markers such as CD5, CD24, CD25, CD86, CD38, CD45, CD70, or CD69 could be used to either deplete or enrich for the desired population of cells. Thus, depending on the donor's history of exposure to the antigen (e.g. viral, bacterial, parasite), the antibody titer, total B cells, CD22 enriched B cells, or further enriched B cell subpopulations such as CD27 positive B cells can be used.

EBV Transformation of B Cells

The selected and stimulated population of cells that express antibodies having specific isotypes can be immortalized using a viral immortalizing agent. Different immortalizing agents can be used on antibody-secreting cells to obtain immortalized antibody-secreting cells.

Among the viral immortalizing agents, a virus that infects and immortalizes antibody-secreting cells can be preferably used in the practice of the invention. Commonly used viruses are lymphotropic viruses, grouped in the gamma class of herpesvirus. Members of this virus family infect lymphocytes in a species-specific manner, and are associated with lymphoproliferative disorders and the development of several malignancies (Nicholas J, 2000; Rickinson A, 2001).

EBV (Epstein-Barr virus, also known as herpesvirus 4), and HHV-8 (human herpesvirus 8, also known as KSHV, Kaposi's Sarcoma associated Herpervirus) infect and immortalize human lymphocytes. MHV-68 (murine herpesvirus 68), HVS (herpesvirus Samiri), RRV (Rhesus Rhadinovirus), LCV (primate Lymphocryptovirus), EHV-2 (Equine Herpesvirus 2) HVA (Herpesvirus Ateles), and AHV-1 (Alcelaphine Herpesvirus 1) are other oncogenic, lymphotropic herpesvirus having common genetic features conserved among them and similar pathogenic effects in different mammalian host cells. These viruses can be used in practice of the present invention.

In addition to the use of intact viruses, recombinant DNA constructs that contain specific viral proteins have been successfully used to immortalize B cells (Damania B 2004; Kilger E et al., 1998). Vectors containing viral genes can be transduced into cells, sometimes making use of retroviral systems or packaging cell lines which provide all the necessary factors in trans for the formation of such virus-like particles, can also be used in the methods of the invention.

EBV-mediated immortalization is a complex process involving the immortalization of B cells due to proteins that are expressed by EBV, and is regulated by the interaction between EBV and host cells proteins (Sugimoto M et al., 2004; Bishop G E, and Busch L K, 2002). If desired, the immortalization process can be followed by measuring the expression of specific EBV proteins and transcripts such as EBNA2, EBNA1, LMP2, LMP1, or EBERs (Thorley-Lawson D A, 2001). These proteins can be detected by PCR, immunofluorescence, Western blot, or other methods allowing the detection of EBV DNA and proteins in infected cells (Schlee M et al., 2004; Park C H et al., 2004; Humme S et al., 2003; Konishi K et al., 2001; Haan K et al., 2001).

Screening and Isolation of Transformed B Cells

In some embodiments, transformed and/or activated B cells can be screened for those having the desired antigen specificity, and individual B cell clones can then be produced from the positive cells. The screening step can be carried out by ELISA, by staining of tissues or cells (including transfected cells), a neutralization assay, and/or one of a number of other methods known in the art for identifying desired antigen specificity. The assay can select on the basis of simple antigen recognition, or can select on the additional basis of a desired function, e.g. neutralizing antibodies rather than just antigen-binding antibodies.

In some embodiments, a cloning step for separating individual clones from the mixture of positive cells can be carried out using limiting dilution, micromanipulation, single cell deposition by cell sorting, and/or by any other method known in the art. In some embodiments, cloning is carried out using limiting dilution. In some embodiments, cloned B cells are derived from B cells that have been immortalized using EBV-transformation coupled with inhibition of host innate response to activator-mediated proliferative signals.

In some embodiments, the present disclosure provides for the production of immortalized B cells that produce antibodies having a desired antigen specificity. Such B cells can be used in various ways, e.g. as a source of monoclonal antibodies, as a source of nucleic acid (DNA or mRNA) encoding a monoclonal antibody of interest, for delivery to subjects for cellular therapy, as a therapeutic or pharmaceutical.

In some embodiments, the supernatant from the activated B cells in culture can be screened for antibodies of interest using known methods known in the art. Screening is performed to identify one or more monoclonal antibodies capable of binding to an antigen of interest. Such screening can be performed on culture supernatant and/or purified antibodies. Alternatively, screening can be carried out using culture supernatant and/or purified antibodies from activated and/or immortalized B cells. In addition, where cross-reactive antibodies are of interest, the ability of the monoclonal antibodies to cross-react with two or more different antigens can be determined. Moreover, in some embodiments, it can be desirable to screen for antibodies with certain functional characteristics (e.g. neutralizing activity).

The binding specificity of monoclonal antibodies produced by the present disclosure can, for example, be determined in an immunoassay, e.g. by immunoprecipitation or other in vitro binding assay, such as radioimmunoassay (RIA) or enzyme-linked immunoadsorbent assay (ELISA).

Representative general classes of screening methods that can be employed include, but are not limited to, (a) antibody capture assays; (b) antigen capture assays; and (c) functional screens.

In antibody capture assays, the antigen can be bound to a solid phase, monoclonal antibodies to be tested are allowed to bind to the antigen, unbound antibodies are removed by washing, and then the bound antibodies are detected, e.g. by a secondary reagent such as a labeled antibody that specifically recognizes the antibody.

For an antigen capture assay, the antigen can be labeled directly. In one embodiment, monoclonal antibodies to be tested can be bound to a solid phase and then reacted with the optionally labeled antigen. Alternatively, the antibody-antigen complex can be allowed to form by immunoprecipitation prior to binding of the monoclonal antibody to be tested to a solid phase. Once the antibody-antigen complexes are bound to the solid phase, unbound antigen can be removed by washing and positives can be identified by detecting the antigen.

Various functional screens exist for identifying monoclonal antibodies with desired activities. In the present disclosure, one such screen, as described in the Examples, is a neutralization assay.

Recombinant Expression

The methods of the present disclosure also provide for obtaining and/or sequencing a nucleic acid for the antibody from the selected B cell clone; and utilizing the nucleic acid to generate a host cell that can express the antibody of interest.

In some embodiments, the nucleotide sequence encoding a desired antibody can be sequenced and thereafter employed in a heterologous expression system, e.g. 293 cells or CHO cells. In some embodiments, an antibody can be recombinantly expressed by obtaining one or more nucleic acids (e.g. heavy and/or light chain genes) from the a B cell clone that encodes the antibody of interest and inserting the nucleic acid into a host cell in order to permit expression of the antibody of interest in that host.

Production of antibodies using recombinant DNA methods is described, for example, in U.S. Pat. No. 4,816,567. For recombinant production of the antibody, the nucleic acid encoding it is isolated and inserted into a replicable vector for further cloning (amplification of the DNA) or for expression. DNA encoding a monoclonal antibody is readily isolated and sequenced using conventional procedures (e.g., by using oligonucleotide probes that are capable of binding specifically to genes encoding the heavy and light chains of the antibody). Vectors that can be used generally include, but are not limited to, one or more of the following: a signal sequence, an origin of replication, one or more marker genes, an enhancer element, a promoter, and a transcription termination sequence. Examples of such expression system components are disclosed in, for example, U.S. Pat. No. 5,739,277. Suitable host cells for cloning or expressing the DNA in the vectors herein are the prokaryote, yeast, or higher eukaryote cells (see, e.g., U.S. Pat. No. 5,739,277).

Pharmaceutical Compositions

The presently disclosed subject matter provides pharmaceutical compositions comprising the antibodies produced in accordance with the present disclosure. In some embodiments, pharmaceutical compositions comprising transformed and/or activated B cells are provided. In some embodiments, a pharmaceutical composition can comprise one or more monoclonal antibodies produced in using the methods disclosed herein. In some embodiments, both monoclonal antibodies as well as the transformed and/or activated B cells of the presently disclosed subject matter can be included in a pharmaceutical composition. In some embodiments, a panel of monoclonal antibodies produced according to the present disclosure can be included in a pharmaceutical composition. In some embodiments, the monoclonal antibodies and/or B cells produced according to the present disclosure can be included with one or more additional agents, for example, antiviral drugs or analgesics.

In some embodiments a pharmaceutical composition can also contain a pharmaceutically acceptable carrier or adjuvant for administration of the antibody. In some embodiments, the carrier is pharmaceutically acceptable for use in humans. The carrier or adjuvant should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated as tablets, pills, dragees, capsules, liquids, gels, syrups, slurries and suspensions, for ingestion by the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) Cancer Res 54:5408-5413; Saltzman & Fung (1997) Adv Drug Deliv Rev 26:209-230), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490,840, and 5,855,900), and a polysome (U.S. Pat. No. 5,922,545).

Antibody sequences can be coupled to active agents or carriers using methods known in the art, including but not limited to carbodiimide conjugation, esterification, sodium periodate oxidation followed by reductive alkylation, and glutaraldehyde crosslinking (Goldman et al. (1997) Cancer Res. 57:1447-1451; Cheng (1996) Hum. Gene Ther. 7:275-282; Neri et al. (1997) Nat. Biotechnol. 15:1271-1275; Nabel (1997) Vectors for Gene Therapy. In Current Protocols in Human Genetics, John Wiley & Sons, New York; Park et al. (1997) Adv. Pharmacol. 40:399-435; Pasqualini et al. (1997) Nat. Biotechnol. 15:542-546; Bauminger & Wilchek (1980) Meth. Enzymol. 70:151-159; U.S. Pat. No. 6,071,890; and European Patent No. 0 439 095).

A therapeutic composition of the present invention comprises in some embodiments a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the present disclosure can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Pharmaceutical compositions can include an effective amount of one or more antibodies as described herein. In some embodiments, a pharmaceutical composition can comprise an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and therapeutics or combination of therapeutics selected for administration. The effective amount for a given situation is determined by routine experimentation as practiced by one of ordinary skill in the art.

Treatment Regimens: Pharmacokinetics

The pharmaceutical compositions of the invention can be administered in a variety of unit dosage forms depending upon the method of administration. Dosages for typical antibody pharmaceutical compositions are well known to those of skill in the art. Such dosages are typically advisory in nature and are adjusted depending on the particular therapeutic context or patient tolerance. The amount antibody adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

For purposes of the present invention, a therapeutically effective amount of a composition comprising an antibody, contains about 0.05 to 1500 μg protein, preferably about 10 to 1000 μg protein, more preferably about 30 to 500 μg and most preferably about 40 to 300 pg, or any integer between these values. For example, antibodies of the invention can be administered to a subject at a dose of about 0.1 μg to about 200 mg, e.g., from about 0.1 μg to about 5 μg, from about 5 μg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg, with optional boosters given at, for example, 1 week, 2 weeks, 3 weeks, 4 weeks, two months, three months, 6 months and/or a year later. It is understood that the specific dose level for any particular patient depends upon a variety of factors including the activity of the specific antibody employed, the age, body weight, general health, sex, diet, time of administration, route of administration, and rate of excretion, drug combination and the severity of the particular disease undergoing therapy.

Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Compositions can be administered in a single dose treatment or in multiple dose treatments on a schedule and over a time period appropriate to the age, weight and condition of the subject, the particular antibody formulation used, and the route of administration.

Kits

The invention provides kits comprising antibodies produced in accordance with the present disclosure which can be used, for instance, for therapeutic applications described above. The article of manufacture comprises a container with a label. Suitable containers include, for example, bottles, vials, and test tubes. The containers can be formed from a variety of materials such as glass or plastic. The container holds a composition which includes an active agent that is effective for therapeutic applications, such as described above. The active agent in the composition can comprise the antibody. The label on the container indicates that the composition is used for a particular therapy or non-therapeutic application, and can also indicate directions for either in vivo or in vitro use, such as those described above.

The following examples of specific aspects for carrying out the present invention are offered for illustrative purposes only, and are not intended to limit the scope of the present invention in any way.

EXAMPLES

Methods and Materials

Ethics Statement

Informed consent was obtained and all procedures carried out under an approved protocol from the National University Institutional Review Board (NUS-IRB number is 06-196).

Cells and Viruses

C6/36 cells and BHK-21 cells were cultured as described previously (28). All dengue strains except EHI and PVP 159 strains were obtained from Novartis Institute of Tropical Diseases, Singapore (NITD). EHI strain was obtained from Environmental Health Institute, Singapore (EHI) and PVP 159 (DENV1/SG/07K3640DK1/2008) from the EDEN patient cohort (29).

Cloning of B Cells

Isolation and immortalization of B cells was carried out as described previously (10). After 15 days of culture, supernatants were screened for DENV-specific antibodies by ELISA and PRNT.

ELISA Binding Assays 96 well flat bottom plates (Maxisorp plates, Nunc) were coated with mouse 4G2 antibody overnight at 5 µg/ml overnight. Plates were washed three times with PBS/Tween-20 0.01%. Different DENV stains were added at $1 \times 10^5$ pfu in 50 ml per well and further incubated for 2 h. Plates were washed three times with PBS/Tween-20 0.01%. HM14C10 was added to the plates and incubated for a further 1 hr. Plates were washed three times with PBS/Tween-20 0.01%. Anti-human IgG conjugated HRP (Pierce, Singapore) was added and incubated for 1 h. TMB substrate (GE healthcare, Singapore) was added and 0.1 M sulphuric acid used to stop the reaction.

Production of Recombinant HM14c10

RNA from B cells was extracted using an RNA extraction kit (Qiagen). The Cloning and expression of recombinant antibodies was conducted as previously described (30).

Antibody-Dependent Enhancement Assay

Dengue virus ($5 \times 10^2$ pfu/ml) was pre-incubated with media, individual monoclonal antibodies (HM4G2, HM14c10 or HM14c10 N297Q) or subclasses of HM14c10 monoclonal antibodies (IgG1, IgG2, IgG3 or IgG4) and then added to $10^5$ of K562 cells. After an hour, cells were washed extensively with PBS to remove unbound virus and monoclonal antibody. After an additional 48 h, supernatants were harvested and viral titers determined by plaque assay on BHK-21 cells.

In Vivo Mouse Experiments

AG129 mice are deficient in IFN-α/β and -γ receptors (31). The mice were handled in accordance with the Institutional Animal Care and Use Committee recommendations (IACUC protocol no: 018/11). A schematic diagram detailing the prophylactic and therapeutic applications of HM14c10 versus PBS treated controls is provided in FIG. 21. Mice were sacrificed and viremia quantified by an established plaque assay (32).

Time-Lapse Confocal Live Cell Imaging

All time-lapse live cell microscopy was performed on an inverted A1Rsi confocal microscope (Nikon, Japan) using Plan-Apochromat 100×1.4 numerical aperture (N.A.) lens. Live cell imaging was performed with living, unfixed BHK cells grown on 25 mm glass coverslips (Marienfeld GmbH, Germany) mounted onto chamber holder (Nikon, Japan). Cells were seeded at a density of $4 \times 10^4$/well 1 day before the experiment and cultured in RPMI 1640 supplemented with 10% FCS. For the simultaneous detection of Alexa Fluor-488 labelled antibodies and Alexa Fluor-647 labelled DEN1 viruses, the 488 nm line of an argon ion laser and the light of a 633-nm helium neon laser were directed over an HFT UV/488/633 beam splitter, and fluorescence was detected using an NFT 545 beam splitter in combination with a 505-530 band pass filter for Alexa Fluor-488 detection and an 650 long pass filter for Alexa Fluor-647 detection. Images were captured at 30 sec intervals at 1 frame per sec (fps) for 30 to 60 min. All live cell imaging experiments were performed using cells incubated at 37° C. in 5% $CO_2$ microscope cage incubator system (OkoLab, Italy). The images were analyzed and processed by Nikon Imaging Software (NIS) elements C software (64 bit, version 3, SP7/build 547) [Nikon, Japan].

Quantification of Intracellular Fluorescence

The effect of antibody on the endocytosis of DENV1 was evaluated by measuring the relative level of fluorescence within the living cells. After treatment with the respective antibody, images of at least 100 cells were randomly acquired using A1Rsi confocal microscope from three independent experiments. The intracellular region of the cells were then individually demarcated manually using the "region of interest" [ROI] function of NIS Elements software (Nikon, Japan) and the relative fluorescence level of Alexa Fluor-488 within each cell was measured using ROI statistics function of the software. The average, standard deviation and student t-test were calculated for each cell population using Microsoft Excel. The fluorescence from untreated cell populations infected with DEN1 were normalized to 100% and used as a comparison to antibody-treated infected cells.

CryoEM

Dengue virus (strain PVP 159) was prepared as described previously (3). Virus was mixed with Fab HM14c10 in a molar ratio of 1:1, incubated at 37° C. for 30 min, and then 4° C. for 2 h. The complex was then flash frozen in liquid ethane on lacey carbon grids, which were coated with a thin layer of continuous carbon. Virus particles were imaged with a 300 kV FEI Titan Krios in the following conditions: electron dose of 16 $e^-/Å^2$, magnification of 47,000, defocus range of 1 μm to 3 μm. The images were recorded on a 4K by 4K Gatan CCD camera resulting in a pixel size of 1.9 Å per pixel. The total of 5,566 particles were boxed and contrast transfer function parameters were determined by using the programs boxer and ctfit, respectively, in the EMAN (33) program suite. Orientation of the particles was determined by using multi-path simulated annealing (MPSA) protocol (34). West Nile virus was used as an initial model (26). The three-dimensional map was generated by using the program make3d in EMAN. The resolution of the final map was found to be 7 Å resolution as determined by the fourier shell coefficient cutoff of 0.5. The DENV1 post-fusion E protein crystal structure (18) does not fit well into the cryoEM density map as a rigid body, the domains in the E protein were thus broken up and then fitted separately. The fit of the molecules into the cryoEM map (set at 4σ contour level) were then optimized by using the "fit-in-map" function of Chimera (35). To create a homology model of HM14c10 variable region, a structure with the best sequence match was chosen (PDB code 2 GHW) and the homology model was created by using the Modeller (19). The heavy and light chain of the homology model were fitted separately into the cryoEM map (set at 3σ contour level) in the two possible orientations of the Fab (FIG. 19).

Example 1

Figure 14:
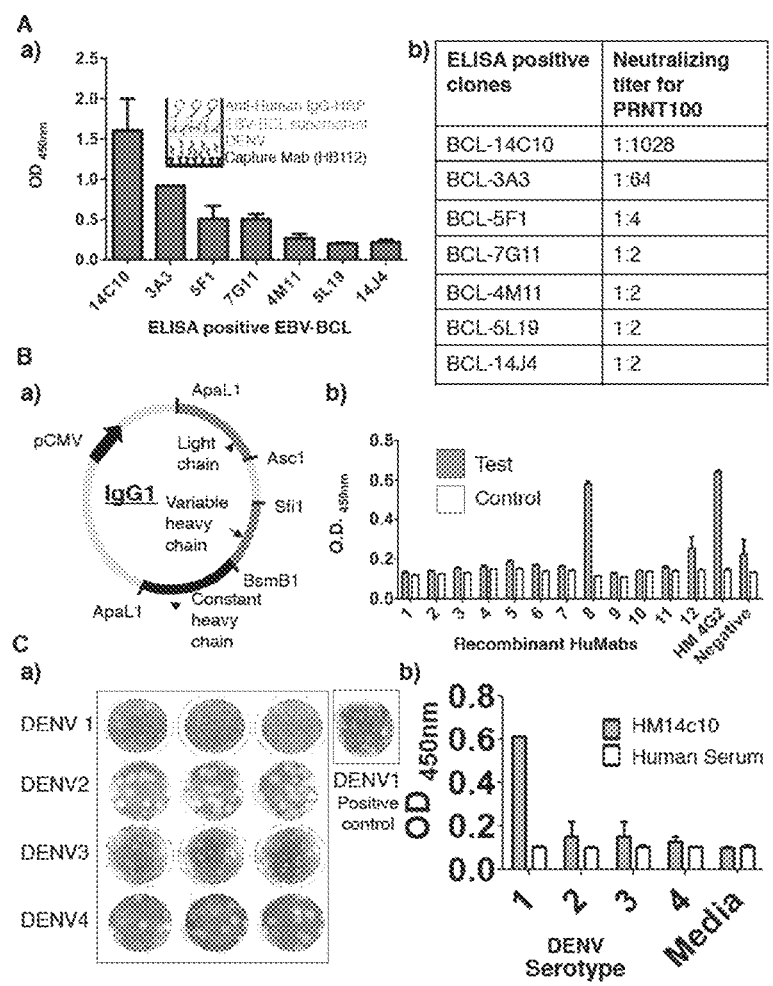
FIG. 14: Identification and recombinant expression of a fully human antibody with neutralizing activity for Dengue Virus. (A)(a) Two thousand EBV-B-cell lines were generated from a DENV1 infected patient and supernatants screened by ELISA for binding activity to DENV1 but not DENV2, 3 or 4. Seven positive EBV-BCL cell lines were identified. (b) A plaque reduction neutralization test (PRNT) was carried out to test for neutralizing activity. The data is expressed as a PRNT100 (i.e. complete neutralization) at the highest dilution factor and is the average value from 3 experiments. (B)(a) Schematic of pTT5 vector utilized to express antibody Heavy Chain and Light Chain templates derived from EBV-BCL in HEK293 cells. (b) Twelve recombinant human IgG1 mAbs were cloned and expressed from the EBV-BCL 14c10 cell line and tested for binding activity to DENV1 by ELISA. A humanized mouse monoclonal 4G2 antibody (HM4G2) was employed as a positive control. Recombinant antibody template number 8 (termed HM14c10) exhibited binding activity for DENV1. (C)(a) PRNT activity of HM on DENV1, 2, 3 and 4. (b) HM14c10 was tested for binding activity to DENV1, 2, 3 and 4 by ELISA. These data represent the mean of 3 experiments and error bars equal standard deviation from the mean of triplicate sample sets.
Figure 15:
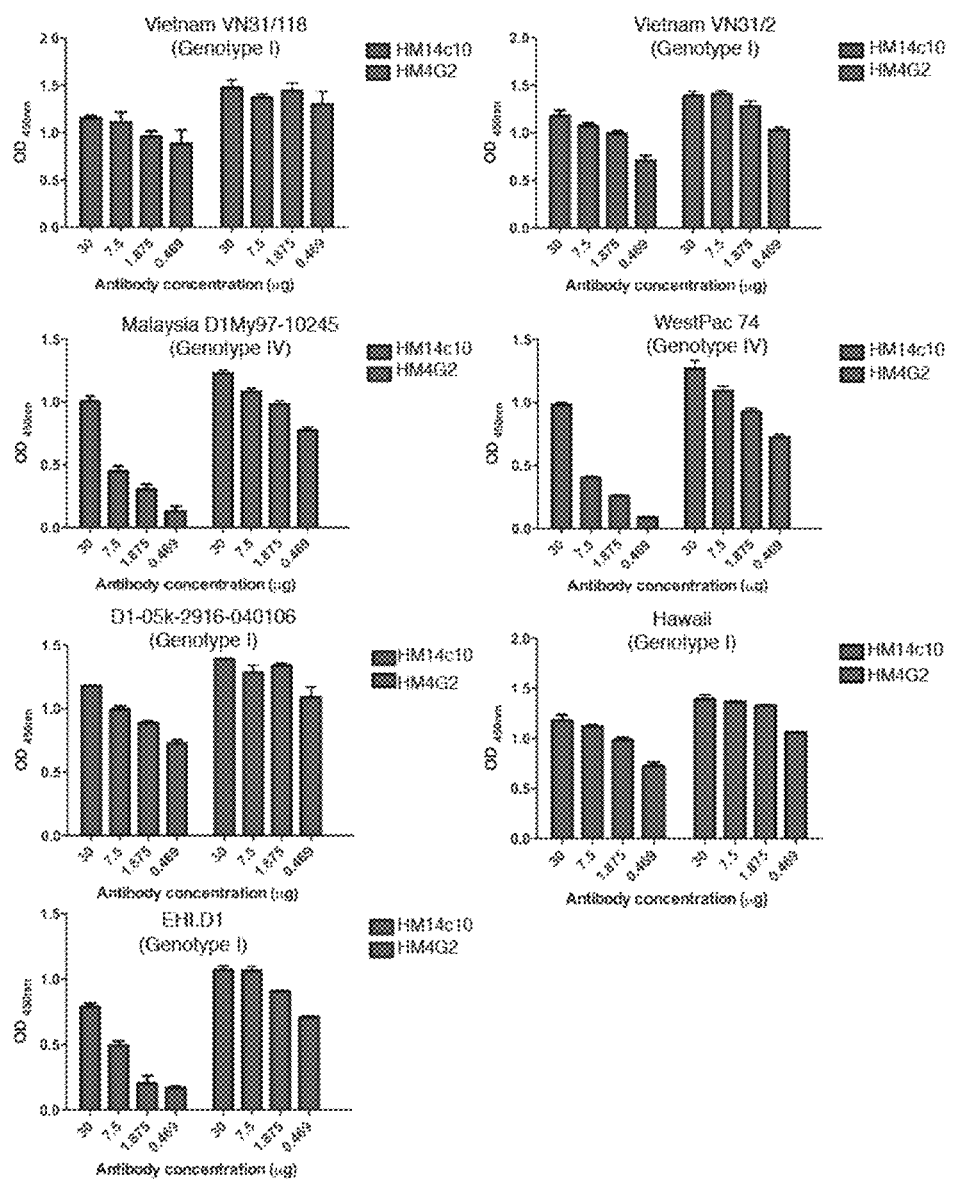
FIG. 15: HM14c10 exhibits binding activity for multiple DENV1 clinical isolates. HM14c10 binding activity for several DENV1 isolates was compared to a humanized mouse monoclonal antibody HM4G2 at various concentrations using an established ELISA protocol. All DENV1 isolates were employed at $1\times10^6$ pfu/ml and coated overnight at 4° C. with HB112 used as a capture reagent. HM or HM4G2 antibody were added at 5 μg/ml and anti-human IgG HRP conjugates were utilized for detection of binding activity.
Figure 16:
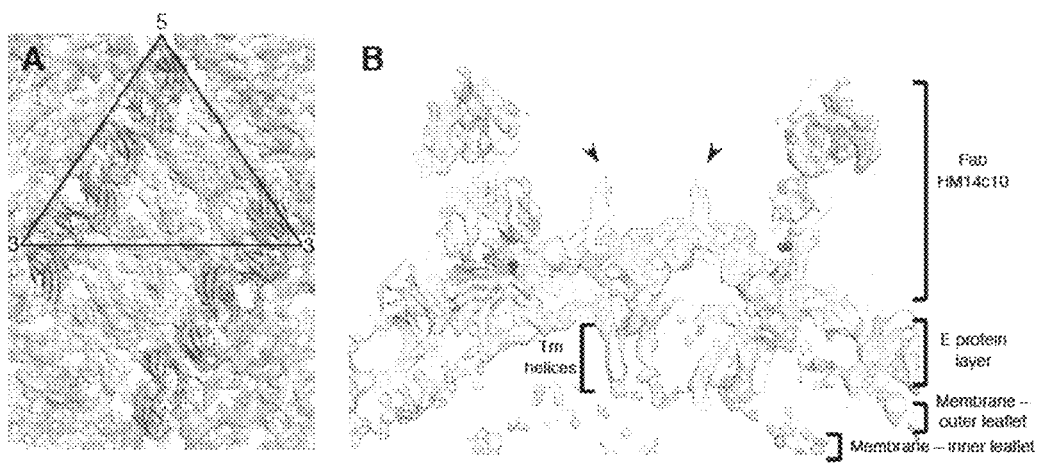
FIG. 16: Fit of the post-fusion crystal structure of DENV1 E proteins into the cryoEM map of Fab HM14c10 complexed with Dengue 1 virus. (A) Top view of the fitted dengue 1 E proteins. The cryoEM map is displayed at a high contour level of 5.5σ so that clear outline of E protein densities can be observed. At this contour level, the Fab densities disappeared, indicating that not all available E protein epitopes are occupied by Fab molecule on the virus surface. The electron densities of the virus surface were interpreted by fitting in the crystal structure of the post-fusion structure of DENV1 E protein (18). Since the crystal structure of the DENV1 post-fusion E protein does not fit well into the cryoEM map as a rigid body, the three domains of the E protein had to be fitted separately. Domains I, II and III of the E protein are colored in red, yellow and blue, respectively. E proteins from two asymmetric units are shown here with one asymmetric unit indicated with a triangle. (B) Side view of the fitted E proteins on the surface of DENV1. Densities of the Fab molecules, E protein ectodomain and transmembrane (Tm) helices can be observed. Densities corresponding to glycans at position Asn159 on two adjacent E proteins are marked with arrowheads and the position of outer and inner leaflet of the lipid bilayer are indicated. The cryoEM map is shown at 2.5σ contour level.
Figure 17:
FIG. 17: Stereo-diagram of the Fab HM14c10 and E protein binding interface. Density of Fab HM14c10(II) shows clear connections to E proteins on the virus surface. Contact residues are indicated with spheres. CryoEM density is shown at 2.5σ contour level.
Figure 18:
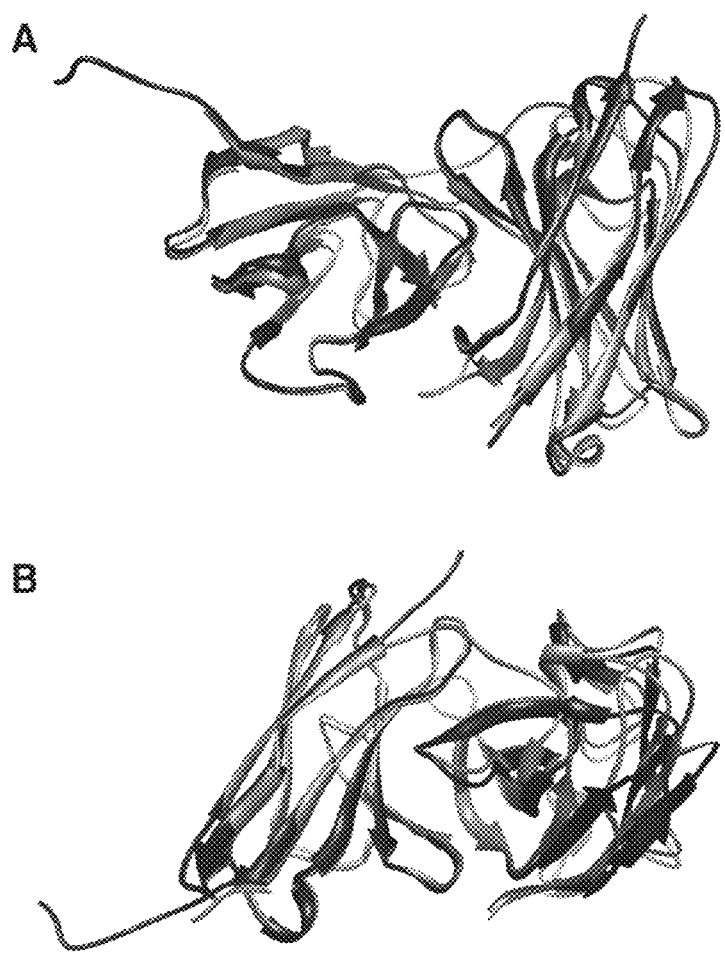
FIG. 18: Superposition of the variable regions of homology model of HM14c10 (green) with reference human monoclonal antibody (PDB code 2 GHW) (blue). Figure is showing (A) side and (B) top view of the antibody variable regions.

Isolation of a Strongly Neutralizing, DENV1 Specific Antibody 14c10 from a Convalescent DENV1 Infected Patient A group of B-lymphocyte cell lines secreting antibodies with serotype-specific binding and neutralizing activity for DENV1 were identified, sub-cloned and expanded. One of these cell lines, BCL-14c10, produced IgG with significantly stronger binding and neutralizing activity than others (FIG. 14A). This cell line was used as a source of immunoglobulin gene templates for PCR amplification and expression of recombinant human IgG1s (FIG. 14B(a)). One recombinant human antibody (HM) 14c10 had comparable binding activity for DENV1 with the parental BCL-14c10 (FIG. 14B(b)). HM14c10 neutralized and bound to DENV1 but not DENV2, 3 or 4 (FIG. 14C), and exhibited strong neutralizing activity with a $PRNT_{50}$ of 0.328 μg/ml in vitro (FIG. 11A).

The ADE activity linked to the development of DHF and DSS has been proposed to occur when sub-neutralizing concentrations of antibodies and DENV form complexes that bind to Fc receptor-bearing cells. This leads to an increase in virus uptake and secretion of pro-inflammatory cytokines and chemokines (11). We compared the ADE activity of HM14c10 with a humanized anti-*Flavivirus* monoclonal antibody HM4G2 using an established in vitro assay employing the FcγR expressing myelomonocytic cell line K562 (12). HM4G2 has cross-serotype binding activity and targets a conserved fusion loop of E-DII on the DENV1-4 (13). We observed that HM14c10 exhibits some homotypic enhancement of DENV1 infection at sub-neutralizing concentrations but no enhancing activity for DENV2, 3 or 4, to which it does not bind. In contrast, HM4G2 mediates enhancement of all four serotypes at sub-neutralizing concentrations (FIG. 11B). To investigate the contribution of K562 FcγRs to the observed homotypic ADE activity of HM14c10, we expressed the antibody as a Fab fragment or reduced FcγR binding by removing the glycosylation site on human IgG1 through substitution of the aspargine residue (N) at position 297 for glutamine (Q) (14). Both the HM14c10Fab and N297Q mutant exhibited a reduction in their homotypic ADE activity versus whole IgG1 controls (FIG. 11C(a)). We next compared the influence of IgG sub-class on ADE activity and observed a partial correlation with the reported binding activities for FcγRIIA on K562 (15). The ADE activity can be ranked as follows: IgG3>IgG1>IgG2>IgG4 with IgG3 being highest and IgG4 the lowest (FIG. 11C(b)). Thus the ADE activity of this neutralizing anti-DENV antibody appears dependent on FcγR binding though it should be noted that the influence of the high affinity FcγR1 and complement components on virus neutralization was not addressed in these experiments (16).

An additional complexity in DENV is the presence of multiple genotypes within a single serotype. DENV1 genotypes can vary up to 3% in their amino acid composition and previous reports of mouse anti-DENV antibodies have suggested that protective activity can vary between genotypes (17). We compared the binding activity of HM14c10 for a number of DENV1 clinical isolates representing two disparate DENV1 genotypes (I and IV) with HM4G2. Both HM14c10 and HM4G2 exhibited binding activity for the genotypes tested, with HM4G2 displaying better binding characteristics in all cases (FIG. 15). In contrast, HM exhibited superior neutralization activity compared to HM4G2 for all of the isolates/genotypes tested (FIG. 11D).

Example 2

HM14c10 Binds a Quaternary Structure Dependent Epitope

The exact nature of the interaction between a given antibody and the DENV must hold the key to explaining neutralization. To determine this, a cryo-electron microscopy (cryoEM) structure of Fab HM14c10:DENV1 complex was solved to 7 Å resolution (FIG. 12A). At full occupancy, 120 copies of Fab HM14c10 bind to all of the available 180 copies of E proteins on the virus surface. To identify the footprint of HM on E protein, the crystal structure of DENV1 E protein (18) was fitted into the cryoEM density map (FIG. 16 and Table 1). The 7 Å resolution cryoEM map showed clear density connections between the HM Fabs and the E proteins, allowing the identification of E protein residues at the interacting interface (FIG. 12B and FIG. 17). The epitope recognized by HM is dependent on the quaternary structure of the virus. Two Fabs of HM bind to three E proteins in the virus asymmetric unit (FIGS. 12C and D). Each antibody binds across two adjacent E proteins with half of the epitope on E-DIII and the other half on E-DI and the E-DI-E-DII hinge of a neighboring E protein.

To understand the Fab interaction with the E protein, a homology model of the variable region of HM14c10 was created (FIG. 18) based on a reference human antibody structure (PDB code 2 GHW) by using the Modeller (19). The variable region of the light and heavy chain of the homology model were then fitted into the cryoEM densities. Although the structures of both chains are similar, there is a distinctive fit that gives a better correlation to the density (FIGS. 19A and B). Analysis of the Fab-E protein interface suggests that all complementarity determining regions (CDR) of the heavy and light chains are involved in the interaction (Fig. S6C).

TABLE 1

Fitting of DENV 1 E protein domains into HM14c10:DENV1 cryoEM density.

| E protein in asymmetric unit[a] | E protein domain | Number of fitted atoms | Average map value at atom positions before[b]/after fitting[c] | Number of atoms outside contour before[b]/after fitting[c] | Shift from previous position (Å) | Rotation from previous position (°) |
|---|---|---|---|---|---|---|
| A | I | 889 | 3.790/4.291 | 447/362 | 2.63 | 16.1 |
|   | II | 1,260 | 4.635/5.212 | 533/424 | 2.16 | 3.02 |
|   | III | 1,522 | 3.592/4.141 | 816/695 | 2.98 | 6.07 |
| B | I | 889 | 4.126/4.368 | 403/368 | 1.37 | 12.7 |
|   | II | 1,260 | 4.715/5.359 | 539/409 | 2.30 | 4.51 |
|   | III | 1,522 | 4.185/4.380 | 685/648 | 1.48 | 4.75 |
| C | I | 889 | 4.033/4.261 | 407/379 | 1.93 | 10.2 |
|   | II | 1,260 | 4.744/5.098 | 499/428 | 1.06 | 7.37 |
|   | III | 1,522 | 4.100/4.345 | 739/668 | 1.64 | 6.03 |

Figure 12:
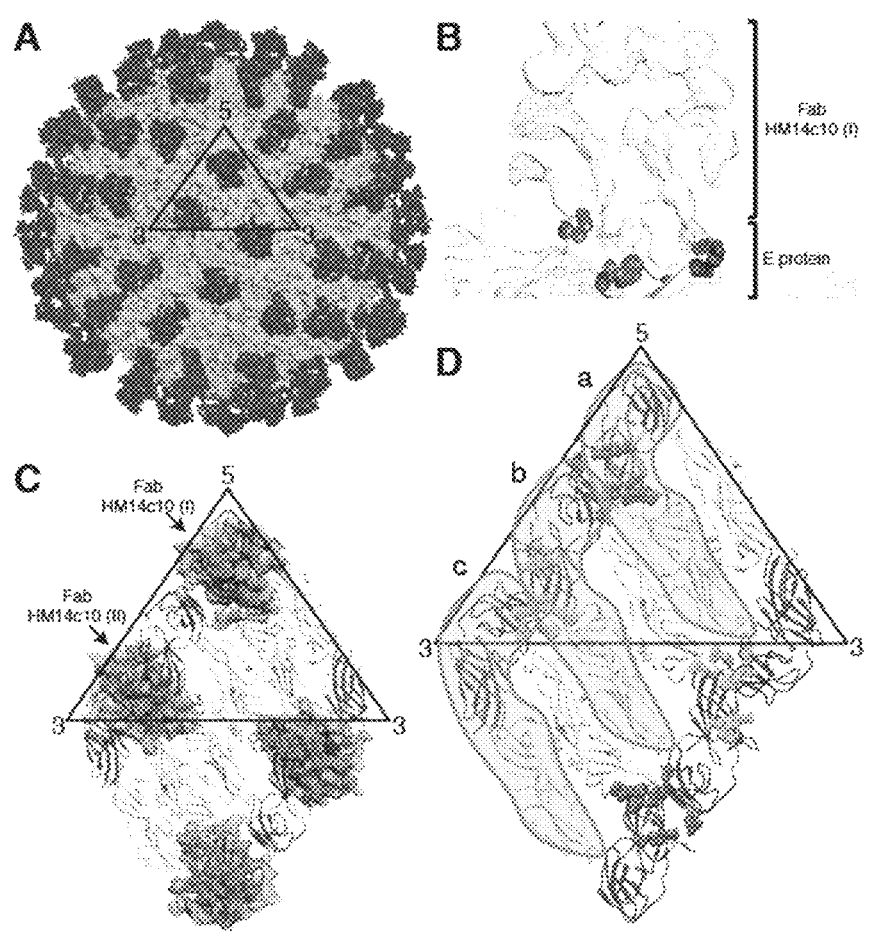
FIG. 12: HM14c10 binds a virus quaternary structure-dependent epitope. (A) CryoEM map of Fab 14c10:DENV1 complex showing 120 Fabs (blue) binding to 180 E proteins on virus surface (cyan). Black triangle represents an asymmetric unit. (B) View of connecting densities of Fab HM14c10(I) to E protein epitope (purple spheres). E protein E-DI, E-DII and E-DIII are colored in red, yellow and blue, respectively. (C) Densities of Fab molecules on E protein Cα chains in two asymmetric units. Fab HM14c10(I) and HM14c10(II) are the two independent molecules in an asymmetric unit. (D) Epitopes of Fab HM14c10(I) (purple spheres) and HM14c10(II) (cyan spheres) on the three E proteins (shaded in grey) in an asymmetric unit.

[a]For designation of E protein position see FIG. 12.
[b]Dengue 1 E protein domains were first superimposed onto the E protein positions of the cryoEM structure of mature dengue 2 virus (27).
[c]The fit of dengue 1 E protein domains into the HM14c10:DENV1 cryoEM map (set at a contour level of 4σ) were optimized by using the fit-in-map function in Chimera (35).

The binding footprints of the two HM14c10 Fabs in an asymmetric unit are not identical (FIG. 12D), with twelve amino acids common to both interfaces but four that are unique (Table 2). Sequence comparison of the epitope residues between different DENV1 isolates indicates that most residues are conserved (FIG. 20A), consistent with the observed neutralizing activity of HM14c10. In contrast, these residues are not conserved in other DENV serotypes or West Nile virus (WNV) (FIG. 20B).

TABLE 2

Fab HM14c10 epitope on DENV 1 E proteins.

| Fab | E protein molecule in the asymmetric unit | E protein domain | E protein residues* |
|---|---|---|---|
| HM14c10(I) | A | I | T51, L135, K136, G159, T160, T165, P166, Q167, E172, I173, T275 |
|   | A | II | N52, G274 |
|   | B | III | K310, E384, K385 |
| HM14c10(II) | B | I | T51, Q131, Y132, G159, T160, T165, P166, Q167, E172, I173, L175, T275 |
|   | B | II | N52, G274 |
|   | C | III | L308, K310 |

*Residues common in both epitopes bound by Fab HM14c10(I) and HM14c10(II) are indicated in bold.

Example 3

Time Lapse Confocal Microscopy Reveals the Neutralization Mechanism of HM14c10

Figure 13:
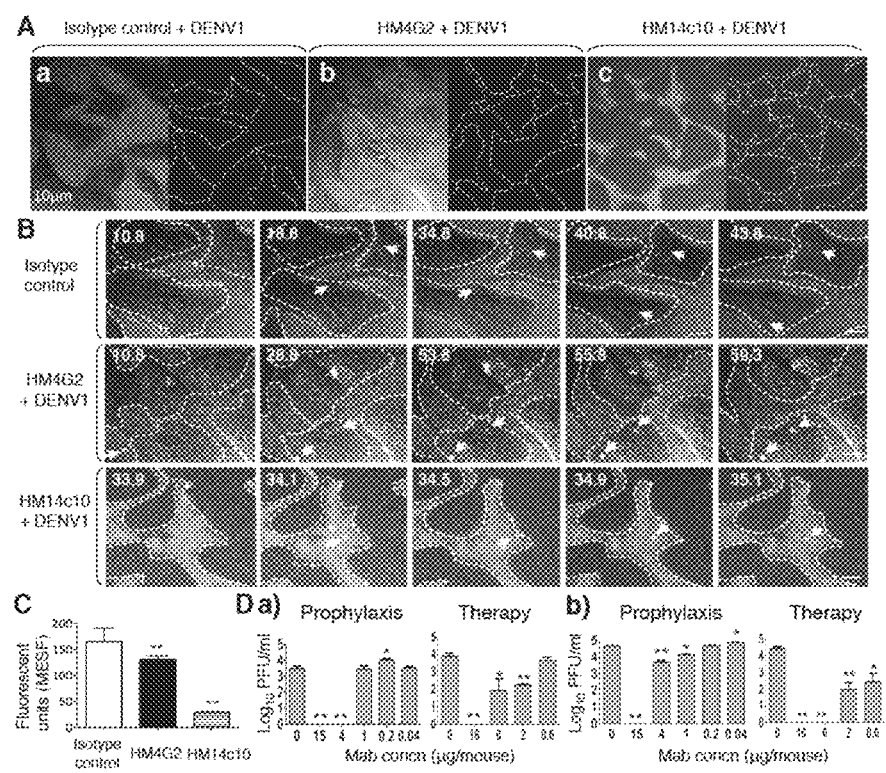
FIG. 13: HM14c10 blocks DENV1 attachment to BHK cells and exhibits potent protective activity in vivo. (A) Time lapse confocal microscopy demonstrating DENV1 infection of BHK host cells in the presence of (a) Isotype control mAb, (b) HM4G2 and (c) HM mAb. Left panels: DENV1 and Mabs were labeled with Alexafluor-647 (red) and Alexafluor-488 (green), respectively. Right panels showing cell boundaries (white dotted lines) and the distribution of DENV1 in cells. (B) Close-up of live infection events. DENV1 are observed inside BHK cells from 18 min in the isotype controls and from 28 min with HM4G2. HM14c10:DENV1 complexes are unable to attach to BHK cells. (C) Internal red fluorescence intensity of 120 randomly selected cells quantified as a measure of virus internalization over 1 h. 1-way ANOVA utilized for comparison of 3 groups. $p<0.0001$. (D) HM14c10 is tested for use as a prophylaxis and therapeutic agent; antibody is administered to DENV1 infected AG129 mice at day 0 and day 2 post-infection, respectively. HM14c10 showed protective response whether the virus is injected (a) sub-cutaneously or (b) intraperitoneally. Level of blood viremia is assayed at day 3 or 4 respectively post infection by plaque assay. N=5 in both models and T-test employed for comparison of sample sets,  $p<0.0001$, * $p<0.05$ compared with PBS controls.

Antibodies can neutralize viral infections by diverse mechanisms including inhibition of virus attachment or fusion to endosomal membranes, or through blocking virally-induced conformational changes of the surface glycoproteins (20, 21). To understand the mechanism of HM14c10 neutralization of DENV1, time lapse confocal microscopy was employed to track the infection of cells by live, fluorescently tagged DENV (22) (FIGS. 13 and 21A). When BHK cells were incubated with DENV1 and isotype control Mabs (non-DENV binding), the virus coalesced in multiple, predominantly perinuclear, intra-cellular compartments (FIG. 14A (a)). Neutralizing concentrations of HM4G2 induced the formation of viral aggregates in the extracellular space but these were also successfully internalized, confirming that HM4G2 does not inhibit virus attachment/internalization (FIG. 13A(b)). In contrast, HM induced the formation of smaller aggregates, but efficiently blocked attachment, with most of the small viral particles remaining in the extracellular space after one hour (FIG. 13A(c)). HM4G2 delayed the accumulation of intracellular viruses compared to the isotype control (FIG. 13B, upper and middle panels). HM14c10: DENV1 complexes failed to enter cells but could be seen deflecting from their surface (FIG. 13B, lower panel). The degree of fluorescent DENV1 internalized under all three conditions was quantified (FIG. 13C). These data suggest that the primary mode of inhibition of DENV1 by HM14c10 is through a blockage of virus attachment to host cells.

Example 4

HM14c10 Exhibits Great Prophylactic and Therapeutic Activity In Vivo

DENV is not a natural pathogen in immunocompetent rodents, it is possible to induce a dose-dependent viremia in AG129 mice deficient in receptors for Type I/II IFN. We injected these mice with unmodified DENV1 subcutaneously (model I, FIG. 21B(a)) or intraperitoneally (model II, FIG. 21B(b)) then quantified viremia 3-4 days later respectively (20). Two DENV1 clinical isolates, representing disparate genotypes (EHI-D 1 genotype I versus Westpac genotype IV), were utilized to determine the in vivo efficacy of HM14c10. In both models, HM14c10 prevented disease when given to mice 24-hours before DENV1 infection, or when given 48 h after infection (FIG. 13D). The lowest concentration of HM14c10 where a significant reduction in viremia was observed is 0.6 μg per mouse (or 160 pM), representing an in vivo potency that has not been matched by any other reported anti-DENV therapeutic formulation.

DISCUSSION

Recent reports on the humoral responses engendered by DENV infection (23, 24) suggest that there is a dominance of antibodies that are mostly DENV serotype cross-reactive with weak neutralization activities. Although scarce in the human serum repertoire, E-DIII antibodies are suggested to protect against DENV infection (23, 24) and this is consistent with studies on the murine antibody response to DENV (7). The Human antibodies characterized have principally been specific for DI and DII of the virus E protein. A small number of characterized antibodies were observed to bind to the whole virus but not to recombinant E protein suggesting specificity for quaternary structure dependent epitopes (23). In this study, we have isolated and thoroughly characterized a potent neutralizing antibody against DENV serotype 1. This antibody is highly neutralizing in both in vitro and in vivo systems. Since it binds only to DENV1, it does not cause enhanced infection of myelomonocytic cells by other DENV serotypes.

Figure 22A:
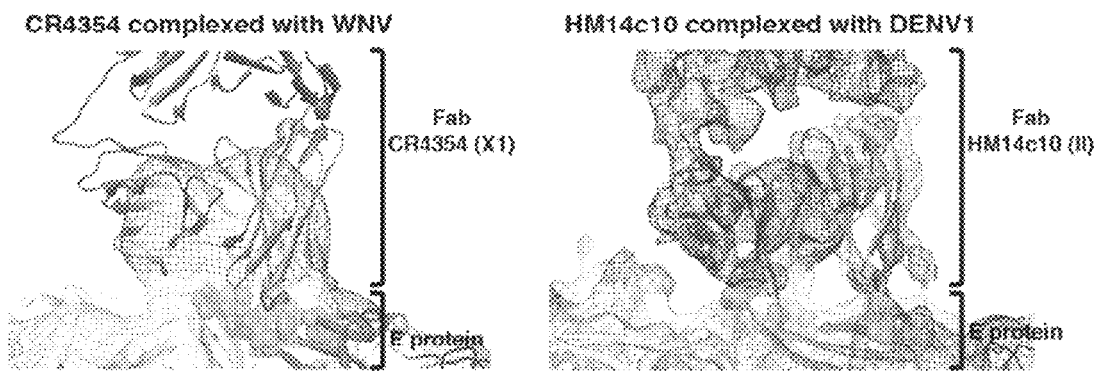
FIG. 22: Comparison of epitope bound by a West Nile virus antibody CR4354 and dengue 1 specific HM14c10. (A) Fit of HM CR4354 and HM 14c10 to E proteins on WNV (left) (25) and DENV (right), respectively. CryoEM density is displayed at 2.8σ (CR4354:WNV) or 2.5σ (HM14c10:DENV1) contour level. (B) An asymmetric unit of WNV (left) and DENV1 (right) with antibody CR4354 or HM14c10 footprints shown in spheres. Epitopes at the two independent binding sites in an asymmetric unit are colored in purple and cyan. The three E proteins in an asymmetric unit are shaded in gray. An asymmetric is shown as black triangle. (C) Comparison of residues in the two independent epitopes (a and b) between CR4354 (on WNV; SEQ ID NO:42) and HM 14c10 (on DENV; SEQ ID NO:33). Residues in the two independent epitopes are colored as in (B).
Figure 22B:
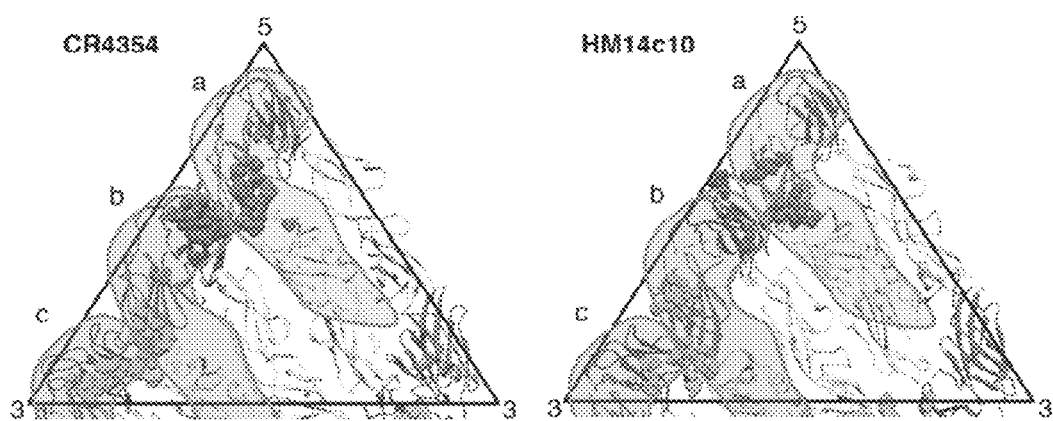

The 7 Å resolution cryoEM structure of Fab HM complexed with DENV1, showed details of the binding between Fab and the E protein. This level of detail has not been observed in the previous cryoEM structures of antibody-*Flavivirus* complexes. The footprint of HM14c10 spans across E-DIII and E-DI:E-DII from a neighboring E protein (FIG. 12D). A report on a human antibody CR4354 specific for WNV has also implicated this region as a target for immunity (25). Although the cryoEM structure of WNV complexed with Fab CR4354 is solved to a lower resolution (14 Å resolution) (FIG. 22A), the fitting of Fab CR4354 crystal structure generates a pseudo-atomic resolution structure. This allowed identification of interacting residues. Comparison of CR4354 epitope on WNV and HM14c10 epitope on DENV1 (FIG. 22B) showed that CR4354 has a bigger proportion of the footprint on E-DIII whereas HM has most of the interacting residues on E-DI. Sequence comparison of the epitopes showed that only approximately 20% of the CR4354 overlaps with HM epitopes, and the overlapping residues are mostly non-conserved (FIG. 22C).

Although CR4354 and HM14c10 epitopes are not identical, the binding of these antibodies should hold the neighboring E proteins together thereby locking the virus structure and preventing the conformation changes essential for a productive infection i.e., virus attachment to host receptors and fusion within the host cells endocytic pathway. Time-lapse live imaging confocal microscopy shows that HM14c10 inhibits the attachment of DENV to host cells. In contrast CR4354 was shown to preferentially inhibit WNV fusion suggesting that targeting this region by antibodies results in more than one mechanism of inhibition.

The surface proteins of DENV have been suggested to undergo constant changes at physiological condition—termed "breathing" (21). It is possible that breathing may play a role in facilitating attachment of the virus to cells. Since HM14c10 cross-links surface E proteins, it may then inhibit attachment by preventing the surface proteins from undergoing breathing. Alternatively, E-DIII has been shown to be important for host cell attachment, the binding of HM14c10 to E-DIII may thus sterically hinder this process. HMAb CR4354, although binding to similar region as HM14c10, does not inhibit WNV attachment. This implies that the encephalitis causing WNV and febrile illness causing DENV do not share identical receptor binding determinants.

HMAb CR4354 was shown to prevent fusion of virus to the endosomal membrane at low pH (25). Since HM14c10 also binds across neighboring E proteins, the possibility that HM may inhibit the rearrangement of dimeric E to trimeric structures during fusion cannot be ruled out. The potential to inhibit both receptor binding and fusion may explain the exceptional in vivo efficacy of HM14c10.

Most *flaviviruses* E-proteins have similar quaternary structure based on a high degree of similarity between the cryoEM structures of WNV (26) and DENV (27). Therefore, all *flavivirus* surface E proteins may undergo similar structural rearrangements during their infection cycle. Antibodies that target a similar region as HM14c10 or CR4354 in other *flaviviruses* may therefore be protective. Since HM14c10 and CR4354 antibodies are the only two antibodies characterized with this binding activity and both are derived from human sources, it indicates that this type of epitope is probably a determinant for generalized *Flavivirus* immunity. This has important implications for the design and evaluation of future vaccines.

Finally, given that HM14c10 has strong neutralization profiles against most clinical DENV1 isolates and excellent in vivo efficacy, this antibody represents a good therapeutic candidate for the treatment of DENV1 infected patients.

REFERENCES

1. S. B. Halstead, E. J. O'Rourke, Dengue viruses and mononuclear phagocytes. I. Infection enhancement by non-neutralizing antibody. *J Exp Med* 146, 201-217 (1977).
2. A. B. Sabin, Research on dengue during World War II. *Am J Trop Med Hyg* 1, 30-50 (1952).
3. R. J. Kuhn, W. Zhang, M. G. Rossmann, S. V. Pletnev, J. Corver, E. Lenches, C. T. Jones, S. Mukhopadhyay, P. R. Chipman, E. G. Strauss, T. S. Baker, J. H. Strauss, Structure of dengue virus: implications for *flavivirus* organization, maturation, and fusion. *Cell* 108, 717-725 (2002).
4. F. A. Rey, F. X. Heinz, C. Mandl, C. Kunz, S. C. Harrison, The envelope glycoprotein from tick-borne encephalitis virus at 2 A resolution. *Nature* 375, 291-298 (1995).
5. Y. Zhang, W. Zhang, S. Ogata, D. Clements, J. H. Strauss, T. S. Baker, R. J. Kuhn, M. G. Rossmann, Conformational changes of the *flavivirus* E glycoprotein. *Structure* 12, 1607-1618 (2004).
6. G. D. Gromowski, A. D. Barrett, Characterization of an antigenic site that contains a dominant, type-specific neutralization determinant on the envelope protein domain III (ED3) of dengue 2 virus. *Virology* 366, 349-360 (2007).
7. S. Sukupolyi-Petty, S. K. Austin, W. E. Purtha, T. Oliphant, G. E. Nybakken, J. J. Schlesinger, J. T. Roehrig, G. D. Gromowski, A. D. Barrett, D. H. Fremont, M. S. Diamond, Type- and subcomplex-specific neutralizing antibodies against domain III of dengue virus type 2 envelope protein recognize adjacent epitopes. *J Virol* 81, 12816-12826 (2007).
8. C. M. Midgley, M. Bajwa-Joseph, S. Vasanawathana, W. Limpitikul, B. Wills, A. Flanagan, E. Waiyaiya, H. B. Tran, A. E. Cowper, P. Chotiyarnwon, J. M. Grimes, S. Yoksan, P. Malasit, C. P. Simmons, J. Mongkolsapaya, G. R. Screaton, An in-depth analysis of original antigenic sin in dengue virus infection. *J Virol* 85, 410-421.
9. W. M. Wahala, A. A. Kraus, L. B. Haymore, M. A. Accavitti-Loper, A. M. de Silva, Dengue virus neutralization by human immune sera: role of envelope protein domain III-reactive antibody. *Virology* 392, 103-113 (2009).
10. E. Traggiai, S. Becker, K. Subbarao, L. Kolesnikova, Y. Uematsu, M. R. Gismondo, B. R. Murphy, R. Rappuoli, A. Lanzavecchia, An efficient method to make human monoclonal antibodies from memory B cells: potent neutralization of SARS coronavirus. *Nat Med* 10, 871-875 (2004).
11. S. B. Halstead, Neutralization and antibody-dependent enhancement of dengue viruses. *Adv Virus Res* 60, 421-467 (2003).

12. R. Littaua, I. Kurane, F. A. Ennis, Human IgG Fc receptor II mediates antibody-dependent enhancement of dengue virus infection. *J Immunol* 144, 3183-3186 (1990).
13. J. T. Roehrig, R. A. Bolin, R. G. Kelly, Monoclonal antibody mapping of the envelope glycoprotein of the dengue 2 virus, Jamaica. *Virology* 246, 317-328 (1998).
14. J. Lund, G. Winter, P. T. Jones, J. D. Pound, T. Tanaka, M. R. Walker, P. J. Artymiuk, Y. Arata, D. R. Burton, R. Jefferis, et al., Human Fc gamma RI and Fc gamma RII interact with distinct but overlapping sites on human IgG. *J Immunol* 147, 2657-2662 (1991).
15. M. S. Chiofalo, G. Teti, J. M. Goust, R. Trifiletti, M. F. La Via, Subclass specificity of the Fc receptor for human IgG on K562. *Cell Immunol* 114, 272-281 (1988).
16. E. Mehlhop, C. Ansarah-Sobrinho, S. Johnson, M. Engle, D. H. Fremont, T. C. Pierson, M. S. Diamond, Complement protein C1q inhibits antibody-dependent enhancement of *flavivirus* infection in an IgG subclass-specific manner. *Cell Host Microbe* 2, 417-426 (2007).
17. J. D. Brien, S. K. Austin, S. Sukupolyi-Petty, K. M. O'Brien, S. Johnson, D. H. Fremont, M. S. Diamond, Genotype-specific neutralization and protection by antibodies against dengue virus type 3. *J Virol* 84, 10630-10643.
18. V. Nayak, M. Dessau, K. Kucera, K. Anthony, M. Ledizet, Y. Modis, Crystal structure of dengue virus type 1 envelope protein in the postfusion conformation and its implications for membrane fusion. *J Virol* 83, 4338-4344 (2009).
19. N. Eswar, B. Webb, M. A. Marti-Renom, M. S. Madhusudhan, D. Eramian, M. Y. Shen, U. Pieper, A. Sali, Comparative protein structure modeling using Modeller. *Curr Protoc Bioinformatics Chapter* 5, Unit 5 6 (2006).
20. R. Rajamanonmani, C. Nkenfou, P. Clancy, Y. H. Yau, S. G. Shochat, S. Sukupolyi-Petty, W. Schul, M. S. Diamond, S. G. Vasudevan, J. Lescar, On a mouse monoclonal antibody that neutralizes all four dengue virus serotypes. *J Gen Virol* 90, 799-809 (2009).
21. S. M. Lok, V. Kostyuchenko, G. E. Nybakken, H. A. Holdaway, A. J. Battisti, S. Sukupolyi-Petty, D. Sedlak, D. H. Fremont, P. R. Chipman, J. T. Roehrig, M. S. Diamond, R. J. Kuhn, M. G. Rossmann, Binding of a neutralizing antibody to dengue virus alters the arrangement of surface glycoproteins. *Nat Struct Mol Biol* 15, 312-317 (2008).
22. S. L. Zhang, H. C. Tan, B. J. Hanson, E. E. Ooi, A simple method for Alexa Fluor dye labelling of dengue virus. *J Virol Methods* 167, 172-177 (2010).
23. R. de Alwis, M. Beltramello, W. B. Messer, S. Sukupolyi-Petty, W. M. Wahala, A. Kraus, N. P. Olivarez, Q. Pham, J. Brian, W. Y. Tsai, W. K. Wang, S. Halstead, S. Kliks, M. S. Diamond, R. Bark, A. Lanzavecchia, F. Sallusto, A. M. de Silva, In-depth analysis of the antibody response of individuals exposed to primary dengue virus infection. *PLoS Negl Trop Dis* 5, e1188.
24. M. Beltramello, K. L. Williams, C. P. Simmons, A. Macagno, L. Simonelli, N. T. Quyen, S. Sukupolyi-Petty, E. Navarro-Sanchez, P. R. Young, A. M. de Silva, F. A. Rey, L. Varani, S. S. Whitehead, M. S. Diamond, E. Harris, A. Lanzavecchia, F. Sallusto, The human immune response to Dengue virus is dominated by highly cross-reactive antibodies endowed with neutralizing and enhancing activity. *Cell Host Microbe* 8, 271-283.
25. B. Kaufmann, M. R. Vogt, J. Goudsmit, H. A. Holdaway, A. A. Aksyuk, P. R. Chipman, R. J. Kuhn, M. S. Diamond, M. G. Rossmann, Neutralization of West Nile virus by cross-linking of its surface proteins with Fab fragments of the human monoclonal antibody CR4354. *Proc Natl Acad Sci USA* 107, 18950-18955.
26. S. Mukhopadhyay, B. S. Kim, P. R. Chipman, M. G. Rossmann, R. J. Kuhn, Structure of West Nile virus. *Science* 302, 248 (2003).
27. W. Zhang, P. R. Chipman, J. Corver, P. R. Johnson, Y. Zhang, S. Mukhopadhyay, T. S. Baker, J. H. Strauss, M. G. Rossmann, R. J. Kuhn, Visualization of membrane protein domains by cryo-electron microscopy of dengue virus. *Nat Struct Biol* 10, 907-912 (2003).
28. C. Y. Huang, S. Butrapet, D. J. Pierro, G. J. Chang, A. R. Hunt, N. Bhamarapravati, D. J. Gubler, R. M. Kinney, Chimeric dengue type 2 (vaccine strain PDK-53)/dengue type 1 virus as a potential candidate dengue type 1 virus vaccine. *J Virol* 74, 3020-3028 (2000).
29. J. G. Low, E. E. Ooi, T. Tolfvenstam, Y. S. Leo, M. L. Hibberd, L. C. Ng, Y. L. Lai, G. S. Yap, C. S. Li, S. G. Vasudevan, A. Ong, Early Dengue infection and outcome study (EDEN)— study design and preliminary findings. *Ann Acad Med Singapore* 35, 783-789 (2006).
30. B. J. Hanson, A. C. Boon, A. P. Lim, A. Webb, E. E. Ooi, R. J. Webby, Passive immunoprophylaxis and therapy with humanized monoclonal antibody specific for influenza A H5 hemagglutinin in mice. *Respir Res* 7, 126 (2006).
31. M. F. van den Broek, U. Muller, S. Huang, M. Aguet, R. M. Zinkernagel, Antiviral defense in mice lacking both alpha/beta and gamma interferon receptors. *J Virol* 69, 4792-4796 (1995).
32. G. K. Tan, J. K. Ng, S. L. Trasti, W. Schul, G. Yip, S. Alonso, A non mouse-adapted dengue virus strain as a new model of severe dengue infection in AG129 mice. *PLoS Negl Trop Dis* 4, e672 (2010).
33. S. J. Ludtke, P. R. Baldwin, W. Chiu, EMAN: semiautomated software for high-resolution single-particle reconstructions. *J Struct Biol* 128, 82-97 (1999).
34. X. Liu, W. Jiang, J. Jakana, W. Chiu, Averaging tens to hundreds of icosahedral particle images to resolve protein secondary structure elements using a Multi-Path Simulated Annealing optimization algorithm. *J Struct Biol* 160, 11-27 (2007).
35. E. F. Pettersen, T. D. Goddard, C. C. Huang, G. S. Couch, D. M. Greenblatt, E. C. Meng, T. E. Ferrin, UCSF Chimera—a visualization system for exploratory research and analysis. *J Comput Chem* 25, 1605-1612 (2004).
36. Kohler and Milstein. *Continuous culture of fused cells secreting antibody of redefined specificity.* Nature, 1975. 256, pp 495-497,
37. Rosen, A.; Gergely, P.; Jondal, M.; Klein, G. and Britton, S. *Polyclonal Ig production after Epstein-Barr virus infection of human lymphocytes in vitro.* Nature, 1977. 267, p. 52-54, Steinitz, M.; Klein, G.; Koskimies, S, and Makel, O. *EB virus-induced B lymphocyte cell lines producing specific antibody.* Nature, 1977. 269, p. 420-422,
38. Gubler, D. J., *Epidemic dengue/dengue hemorrhagic fever as a public health, social and economic problem in the 21st century.* Trends Microbiol, 2002. 10(2): p. 100-3.
39. Mackenzie, J. S., D. J. Gubler, and L. R. Petersen, *Emerging flaviviruses: the spread and resurgence of Japanese encephalitis, West Nile and dengue viruses.* Nat Med, 2004. 10(12 Suppl): p. S98-109 Gubler, D. J., *Cities spawn epidemic dengue viruses.* Nat Med, 2004. 10(2): p. 129-30.
40. Pinheiro, F. P. and S. J. Corber, *Global situation of dengue and dengue haemorrhagic fever, and its emergence in the Americas.* World Health Stat Q, 1997. 50(3-4): p. 161-9.
41. Ooi, E. E., K. T. Goh, and D. J. Gubler, *Dengue prevention and 35 years of vector control in Singapore.* Emerg Infect Dis, 2006. 12(6): p. 887-93.
42. Edelman, R., *Dengue vaccines approach the finish line.* Clin Infect Dis, 2007. 45 Suppl 1: p. S56-60.

43. Zhang W, Chipman P R, Corver J, Johnson P R, Zhang Y, Mukhopadhyay S, Baker T S, Strauss J H, Rossmann M G, Kuhn R J. Visualization of membrane protein domains by cryo-electron microscopy of dengue virus. Nat Struct Biol, 2003.10(11): p. 907-912.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. An isolated neutralizing monoclonal antibody or fragment thereof that specifically binds to a Dengue virus serotype 1 envelope (E) protein or fragment thereof, wherein the antibody is a human antibody with broadly neutralizing activity that binds across two E proteins in a virus, wherein the binding across two E proteins comprises binding to DI and the hinge between DI and II on one E protein and DIII of a neighboring E protein, and wherein the antibody or fragment thereof binds to amino acids T51, G159, T160, T165, P166, Q167, E172, I173, and T275 of SEQ ID NO:33 in DI, amino acids N52 and G274 of SEQ ID NO:33 in DII, and K310 of SEQ ID NO:33 in DIII.

2. The antibody or fragment thereof according to claim 1, wherein the antibody or fragment thereof is selected from the group consisting of: (a) a whole immunoglobulin molecule; (b) an scFv; (c) a Fab fragment; (d) an F(ab')2; and (e) a disulfide linked Fv.

3. The antibody or fragment thereof according to claim 1, which comprises a heavy chain immunoglobulin constant domain selected from the group consisting of: (a) a human IgM constant domain; (b) a human IgG1 constant domain; (c) a human IgG2 constant domain; (d) a human IgG3 constant domain; (e) a human IgG4 constant domain; and (f) a human IgA1/2 constant domain.

4. The antibody or fragment thereof according to claim 1, which comprises a light chain immunoglobulin constant domain selected from the group consisting of: (a) a human Ig kappa constant domain; and (b) a human Ig lambda constant domain.

5. An antibody or fragment thereof that binds to a Dengue virus serotype 1 envelope protein or fragment thereof, wherein the antibody or fragment thereof comprises a heavy chain sequence comprising the CDR sequences SYGMH (amino acid residues 31-35 of SEQ ID NO:20), VIWYDGSKTYYGDSVKG (amino acid residues 50-66 of SEQ ID NO:20), and GIAGGWAFW (amino acid residues 99-107 of SEQ ID NO:20), and a light chain sequence comprising the CDR sequences RASQNVYSYLG (amino acid residues 24-34 of SEQ ID NO:27), GVTSRAT (amino acid residues 50-56 of SEQ ID NO:27), and QQYAG (amino acid residues 89-93 of SEQ ID NO:27).

6. The antibody or fragment thereof according to claim 5, wherein the antibody or fragment thereof comprises a light chain sequence comprising SEQ ID NO:27.

7. The antibody or fragment thereof according to claim 5, wherein the antibody or fragment thereof comprises a heavy chain sequence comprising SEQ ID NO:20.

8. The antibody or fragment thereof according to claim 5, wherein the antibody or fragment thereof comprises a heavy chain sequence comprising SEQ ID NO:20 and a light chain sequence comprising SEQ ID NO:27.

9. The antibody or fragment thereof according to claim 5, wherein the antibody or fragment thereof specifically neutralizes a serotype 1 Dengue virus.

10. The antibody or fragment thereof according to claim 1, wherein the antibody or fragment thereof specifically neutralizes a serotype 1 Dengue virus.

11. The antibody or fragment thereof according to claim 1, wherein the antibody is 14c10, clone 8.

12. The antibody or fragment thereof according to claim 1, wherein the antibody or fragment thereof binds to an antigen with an affinity constant (KD) of less than $1 \times 10^{-8}$ M.

13. The antibody or fragment thereof according to claim 1, wherein the antibody or fragment thereof binds to an antigen with an affinity constant (KD) of less than $1 \times 10^{-9}$ M.

14. The antibody or fragment thereof according to claim 1, wherein the antibody is derived from a B cell of a patient who has recovered from Dengue virus infection.

15. A pharmaceutical composition comprising the antibody or fragment thereof according to claim 1 and a pharmaceutically acceptable carrier effective to reduce or prevent Dengue virus infection in a subject.

16. The pharmaceutical composition of claim 15, further comprising a second agent.

17. The pharmaceutical composition of claim 16, wherein the second agent is an antiviral drug or analgesic drug.

18. The antibody or fragment thereof of claim 1, wherein the antibody or fragment thereof comprises a heavy chain sequence comprising the CDR sequences SYGMH (amino acid residues 31-35 of SEQ ID NO:20), VIWYDGSKTYYGDSVKG (amino acid residues 50-66 of SEQ ID NO:20), and GIAGGWAFW (amino acid residues 99-107 of SEQ ID NO:20), and a light chain sequence comprising the CDR sequences RASQNVYSYLG (amino acid residues 24-34 of SEQ ID NO:27), GVTSRAT (amino acid residues 50-56 of SEQ ID NO:27), and QQYAG (amino acid residues 89-93 of SEQ ID NO:27).

19. The antibody or fragment thereof according to claim 18, wherein the antibody or fragment thereof comprises a heavy chain sequence comprising SEQ ID NO:20 and a light chain sequence comprising SEQ ID NO:27.

* * * * *